United States Patent
Voss

(10) Patent No.: US 8,894,615 B2
(45) Date of Patent: Nov. 25, 2014

(54) INTRODUCER SHEATH AND METHODS OF MAKING

(71) Applicant: Abbott Vascular Inc., Santa Clara, CA (US)

(72) Inventor: Laveille Kao Voss, Belmont, CA (US)

(73) Assignee: Abbott Vascular, Inc., Santa Clara, CA (US)

( * ) Notice: Subject to any disclaimer, the term of this patent is extended or adjusted under 35 U.S.C. 154(b) by 0 days.

(21) Appl. No.: 13/752,137

(22) Filed: Jan. 28, 2013

(65) Prior Publication Data

US 2013/0138043 A1 May 30, 2013

Related U.S. Application Data

(60) Division of application No. 12/695,961, filed on Jan. 28, 2010, now Pat. No. 8,359,723, which is a continuation-in-part of application No. 11/427,306, filed on Jun. 28, 2006, now abandoned.

(60) Provisional application No. 60/695,602, filed on Jun. 30, 2005.

(51) Int. Cl.
*A61B 17/34* (2006.01)
*A61M 25/00* (2006.01)
*B23P 11/02* (2006.01)

(52) U.S. Cl.
CPC ........ *A61B 17/3415* (2013.01); *A61M 25/0009* (2013.01); *A61M 25/0017* (2013.01); *A61M 25/0023* (2013.01)
USPC ....................................... 604/167.03; 29/450

(58) Field of Classification Search
USPC ............ 604/167.03, 170, 264, 289, 523, 524, 604/526, 527, 530, 532, 158, 164, 1, 604/164.03; 29/450, 428, 453
See application file for complete search history.

(56) References Cited

U.S. PATENT DOCUMENTS

| | | | |
|---|---|---|---|
| 2,548,602 | A | 4/1951 | Greenburg |
| 4,143,853 | A | 3/1979 | Abramson |
| 4,406,656 | A | 9/1983 | Hattler et al. |
| 4,411,655 | A | 10/1983 | Schreck |
| 4,451,256 | A | 5/1984 | Weikl et al. |
| 4,574,173 | A | 3/1986 | Bennett |

(Continued)

FOREIGN PATENT DOCUMENTS

| | | |
|---|---|---|
| EP | 0450221 | 10/1991 |
| JP | 3289967 | 12/1991 |

(Continued)

OTHER PUBLICATIONS

U.S. Appl. No. 13/835,570, Mar. 15, 2013, Voss et al.
U.S. Appl. No. 11/427,301, Mar. 11, 2013, Office Action.
U.S. Appl. No. 60/695,464, Jun. 30, 2005, Rowe.
U.S. Appl. No. 60/695,602, Jun. 30, 2005, Voss.
Richard Vennix, Material properties of PTFE, Engineering Polymers/Polymers Data Sheets, Matbase,<<http://www.matbase.com/material/polymers/engineering/ptfe/properties>>Jan. 25, 2010.

(Continued)

*Primary Examiner* — John C Hong
(74) *Attorney, Agent, or Firm* — Workman Nydegger; Randy Shen

(57) ABSTRACT

An introducer sheath and methods of making the introducer sheath are described. The introducer sheath may include a hub portion and a tubular portion. The hub portion may include a substantially non-planar valve portion in a relaxed state. The valve portion may include an aperture configured to receive a medical device. A hub portion may be formed using a forming device. An aperture may be formed through a distal surface of the valve portion. A valve portion may be formed in a cap defining a cavity sized to elastically receive a proximal end of the hub portion.

11 Claims, 11 Drawing Sheets

(56) References Cited

U.S. PATENT DOCUMENTS

| | | | |
|---|---|---|---|
| 4,596,559 A | 6/1986 | Fleischhacker |
| 4,601,713 A | 7/1986 | Fuqua |
| 4,619,643 A | 10/1986 | Bai |
| 4,747,833 A | 5/1988 | Kousai et al. |
| 4,899,729 A | 2/1990 | Gill et al. |
| 4,950,257 A | 8/1990 | Hibbs et al. |
| 4,983,168 A | 1/1991 | Moorehead |
| 5,106,054 A | 4/1992 | Mollenauer et al. |
| 5,106,368 A | 4/1992 | Uldall et al. |
| 5,176,652 A | 1/1993 | Littrell |
| 5,176,659 A | 1/1993 | Mancini |
| 5,180,372 A | 1/1993 | Vegoe et al. |
| RE34,327 E | 7/1993 | Kreamer |
| 5,244,619 A | 9/1993 | Burnham |
| 5,250,033 A | 10/1993 | Evans et al. |
| 5,320,611 A | 6/1994 | Bonutti et al. |
| 5,423,774 A | 6/1995 | Fischell et al. |
| 5,447,503 A | 9/1995 | Miller |
| 5,464,398 A | 11/1995 | Haindl |
| 5,466,230 A | 11/1995 | Davila |
| 5,558,737 A | 9/1996 | Brown et al. |
| 5,674,240 A | 10/1997 | Bonutti et al. |
| 5,693,025 A | 12/1997 | Stevens |
| 5,749,889 A | 5/1998 | Bacich et al. |
| 5,795,326 A | 8/1998 | Simán |
| 5,823,961 A | 10/1998 | Fields et al. |
| 5,827,227 A | 10/1998 | DeLago |
| 5,910,155 A | 6/1999 | Ratcliff et al. |
| 5,944,691 A | 8/1999 | Querns et al. |
| 5,957,902 A | 9/1999 | Teves |
| 5,964,730 A | 10/1999 | Williams et al. |
| 5,968,009 A | 10/1999 | Simán |
| 5,993,436 A | 11/1999 | Kitou et al. |
| 6,183,443 B1 | 2/2001 | Kratoska et al. |
| 6,190,357 B1 | 2/2001 | Ferrari et al. |
| 6,192,568 B1 | 2/2001 | Kafrawy et al. |
| 6,224,586 B1 | 5/2001 | Stephens |
| 6,280,433 B1 | 8/2001 | McIvor et al. |
| 6,312,374 B1 | 11/2001 | von Hoffmann |
| 6,358,266 B1 | 3/2002 | Bonutti |
| 6,416,499 B2 | 7/2002 | Paul, Jr. |
| 6,419,624 B1 | 7/2002 | Burton et al. |
| 6,450,987 B1 | 9/2002 | Kramer |
| 6,497,721 B2 | 12/2002 | Ginsburg, incapacited et al. |
| 6,616,678 B2 | 9/2003 | Nishtala et al. |
| 6,630,086 B1 | 10/2003 | Goral et al. |
| 6,749,600 B1 | 6/2004 | Levy |
| 6,827,710 B1 | 12/2004 | Mooney et al. |
| 6,887,417 B1 | 5/2005 | Gawreluk et al. |
| 6,945,990 B2 | 9/2005 | Greenan |
| 7,144,386 B2 | 12/2006 | Korkor et al. |
| 7,637,893 B2 | 12/2009 | Christensen et al. |
| 7,699,864 B2 | 4/2010 | Kick et al. |
| 7,727,179 B2 | 6/2010 | Barrett |
| 7,762,995 B2 | 7/2010 | Eversull et al. |
| 7,896,897 B2 | 3/2011 | Gresham et al. |
| 7,974,710 B2 | 7/2011 | Seifert |
| 8,012,127 B2 | 9/2011 | Lieberman et al. |
| 8,359,723 B2 | 1/2013 | Voss |
| 2002/0032459 A1 | 3/2002 | Horzewski et al. |
| 2002/0072768 A1 | 6/2002 | Ginn |
| 2002/0107482 A1 | 8/2002 | Rocamora et al. |
| 2002/0183781 A1 | 12/2002 | Casey et al. |
| 2003/0004537 A1 | 1/2003 | Boyle et al. |
| 2003/0014015 A1 | 1/2003 | Tansey, Jr. et al. |
| 2003/0032941 A1 | 2/2003 | Boyle et al. |
| 2003/0158578 A1 | 8/2003 | Pantages et al. |
| 2004/0102738 A1 | 5/2004 | Dikeman et al. |
| 2004/0153122 A1 | 8/2004 | Palermo |
| 2005/0027257 A1 | 2/2005 | Davey |
| 2005/0059934 A1 | 3/2005 | Wenchell et al. |
| 2005/0080430 A1 | 4/2005 | Wright et al. |
| 2005/0085841 A1 | 4/2005 | Eversull et al. |
| 2005/0131447 A1 | 6/2005 | Wahr et al. |
| 2007/0005001 A1 | 1/2007 | Rowe et al. |
| 2007/0224309 A1 | 9/2007 | Mejlhede et al. |
| 2008/0004569 A1 | 1/2008 | McCrystle et al. |
| 2008/0004571 A1 | 1/2008 | Voss |
| 2008/0051717 A1 | 2/2008 | Voss et al. |
| 2009/0054874 A1 | 2/2009 | Barron et al. |
| 2009/0221965 A1 | 9/2009 | Osypka |
| 2009/0264832 A1 | 10/2009 | Dikeman et al. |
| 2009/0270989 A1 | 10/2009 | Conner et al. |
| 2010/0130937 A1 | 5/2010 | Voss |
| 2010/0130939 A1 | 5/2010 | Voss |
| 2010/0198159 A1 | 8/2010 | Voss |
| 2010/0198160 A1 | 8/2010 | Voss |
| 2010/0268163 A1 | 10/2010 | Rowe et al. |
| 2013/0338595 A1 | 12/2013 | Voss |

FOREIGN PATENT DOCUMENTS

| | | |
|---|---|---|
| WO | WO 98/13083 | 4/1998 |
| WO | WO 98/29026 | 7/1998 |
| WO | WO 2004/37333 | 5/2004 |
| WO | WO 2005/018728 | 3/2005 |
| WO | WO 2007/005584 | 1/2007 |
| WO | WO 2008/02915 | 1/2008 |
| WO | WO 2009/120871 | 10/2009 |

OTHER PUBLICATIONS

Richard Vennix, Material Properties of PMMA, Commodity Polymers/Polymer Data Sheets, Matbase, <<http://www.matbase.com/materials/polymers/commodity/pmma/properties>>Jan. 25, 2010.
U.S. Appl. No. 11/427,301, Apr. 27, 2010, Office Action.
U.S. Appl. No. 11/427,301, Oct. 27, 2010, Office Action.
U.S. Appl. No. 11/427,301, Jun. 8, 2012, Office Action.
U.S. Appl. No. 11/427,306, Feb. 26, 2008, Office Action.
U.S. Appl. No. 11/427,306, Mar. 5, 2009, Office Action.
U.S. Appl. No. 11/427,306, Aug. 21, 2009, Office Action.
U.S. Appl. No. 11/427,306, Apr. 12, 2010, Office Action.
U.S. Appl. No. 11/427,306, Oct. 21, 2010, Office Action.
U.S. Appl. No. 11/427,308, Sep. 29, 2009, Office Action.
U.S. Appl. No. 11/427,308, May 11, 2010, Office Action.
U.S. Appl. No. 11/427,308, Sep. 15, 2010, Office Action.
U.S. Appl. No. 11/427,308, Mar. 29, 2011, Office Action.
U.S. Appl. No. 11/427,308, Oct. 25, 2011, Office Action.
U.S. Appl. No 11/427,308, Jul. 19, 2012, Office Action.
U.S. Appl. No. 11/767,947, Jun. 2, 2009, Office Action.
U.S. Appl. No. 11/767,947, Nov. 12, 2009, Office Action.
U.S. Appl. No. 11/767,947, Mar. 31, 2010, Office Action.
U.S. Appl. No. 11/767,947, Aug. 20, 2010, Office Action.
U.S. Appl. No. 11/767,947, Feb. 3, 2011, Office Action.
U.S. Appl. No. 11/767,947, Jul. 8, 2011, Office Action.
U.S. Appl. No. 11/767,947, Feb. 27, 2012, Office Action.
U.S. Appl. No. 12/695,961, Feb. 13, 2012, Office Action.
U.S. Appl. No. 12/695,961, May 11, 2012, Office Action.
U.S. Appl. No. 12/695,961, Sep. 20, 2012, Notice of Allowance.
U.S. Appl. No. 12/695,969, Jan. 24, 2012, Office Action.
U.S. Appl. No. 12/695,969, Jul. 20, 2012, Office Action.
U.S. Appl. No. 12/695,969, Dec. 24, 2012, Notice of Allowance.
U.S. Appl. No. 12/695,975, Feb. 13, 2012, Office Action.
U.S. Appl. No. 12/695,975, May 11, 2012, Office Action.
U.S. Appl. No. 12/695,975, Oct. 5, 2012, Office Action.
U.S. Appl. No. 12/696,792, Nov. 10, 2011, Office Action.
U.S. Appl. No. 12/696,837, Dec. 19, 2011, Office Action.
U.S. Appl. No. 12/696,837, Jul. 19, 2012, Office Action.
U.S. Appl. No. 12/724,889, Mar. 29, 2012, Office Action.
U.S. Appl. No. 12/724,889, Oct. 26, 2012, Office Action.
U.S. Appl. No. 12/695,969, Apr. 24, 2013, Issue Notification.
U.S. Appl. No. 11/427,308, Apr. 23, 2014, Office Action.
U.S. Appl. No. 12/724,889, Mar. 21, 2014, Office Action.
U.S. Appl. No. 13/892,106, Mar. 26, 2014, Office Action.
U.S. Appl. No. 11/767,947, Nov. 27, 2013, Notice of Allowance.
U.S. Appl. No. 12/695,975, Feb. 25, 2014, Office Action.
U.S. Appl. No. 12/696,792, Dec. 27, 2013, Office Action.

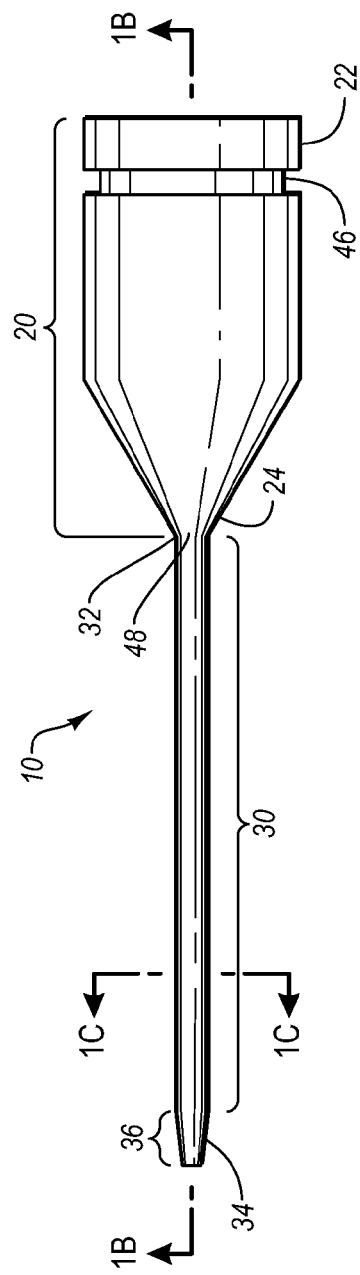
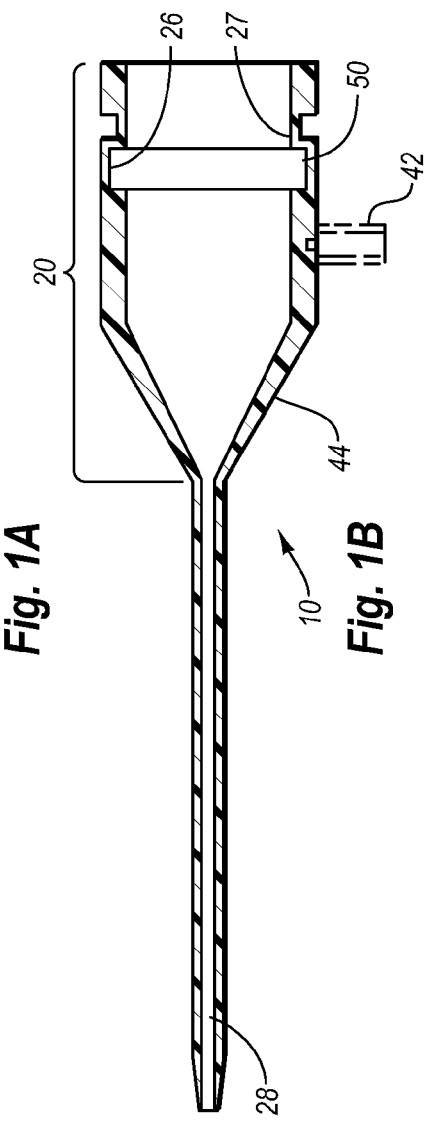
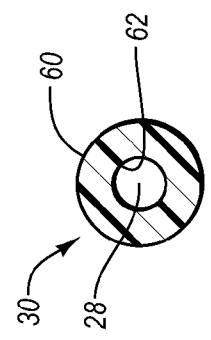
*Fig. 1A*
*Fig. 1B*
*Fig. 1C*

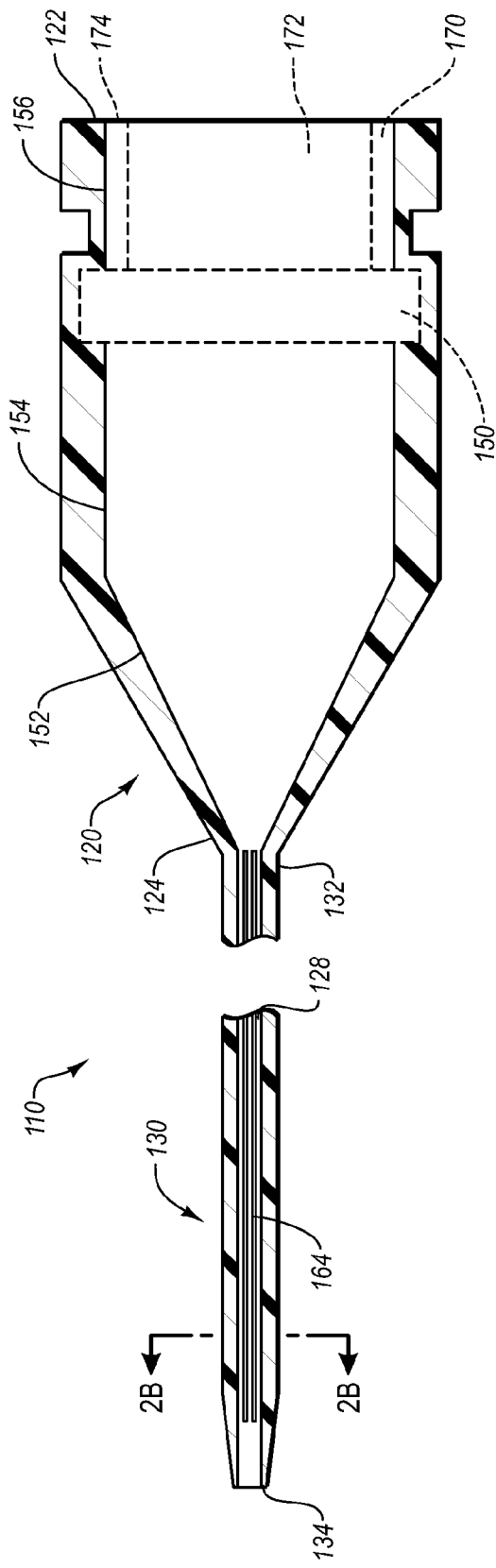
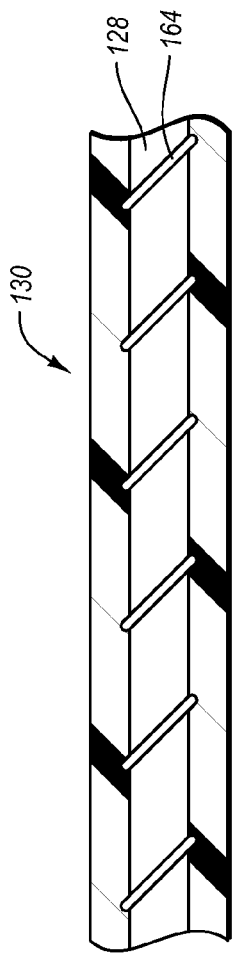
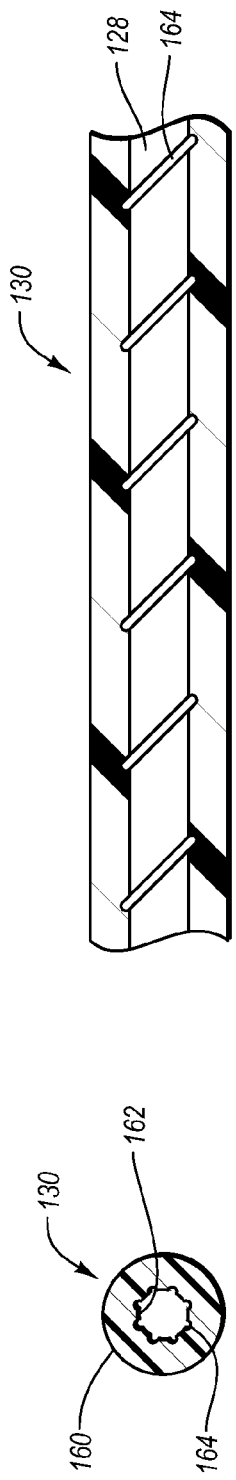
Fig. 2A
Fig. 2B
Fig. 2C

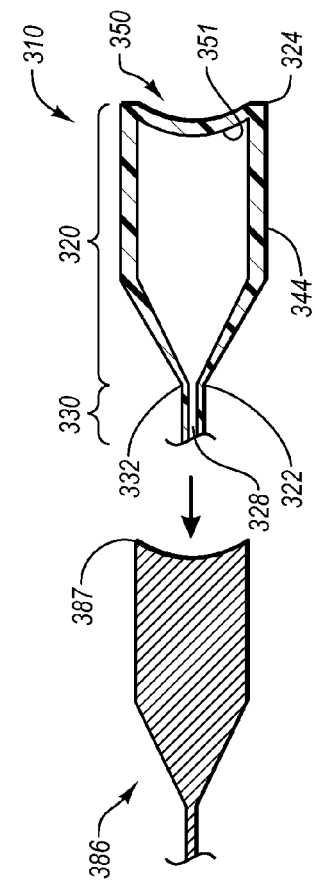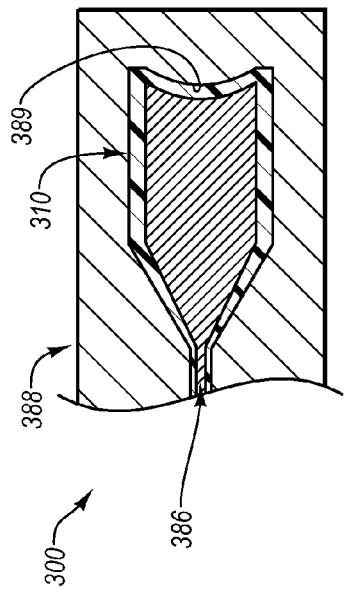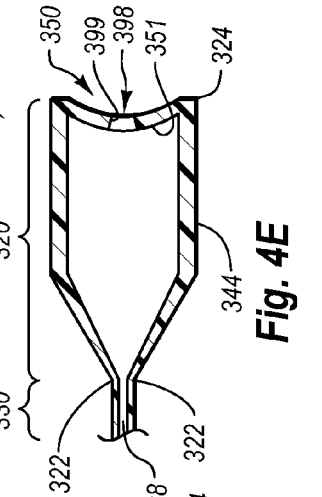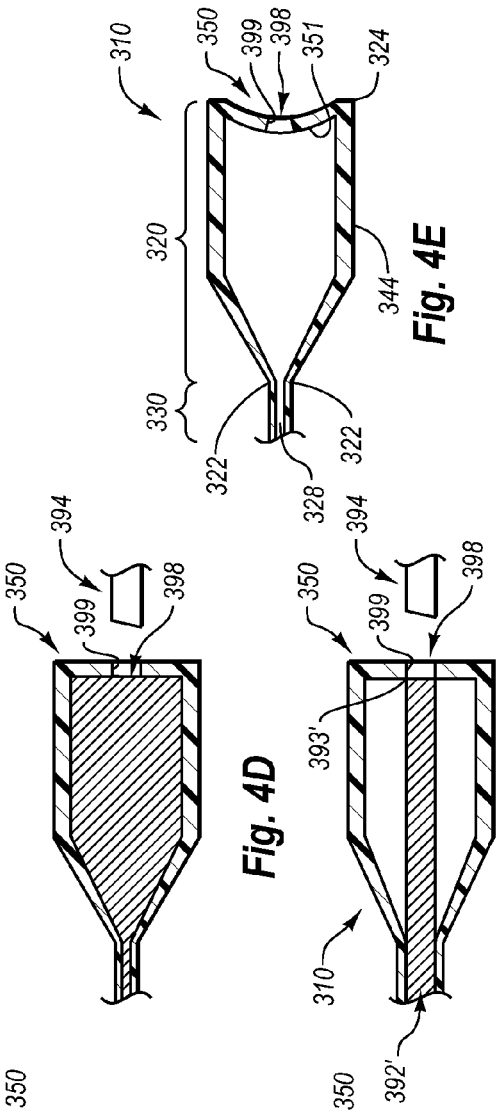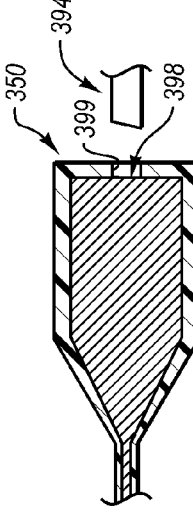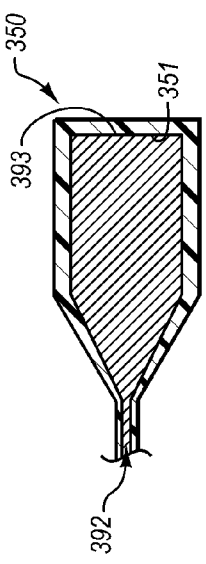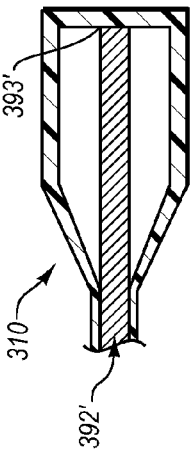

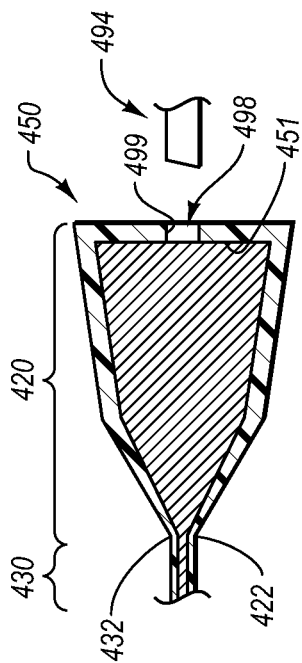
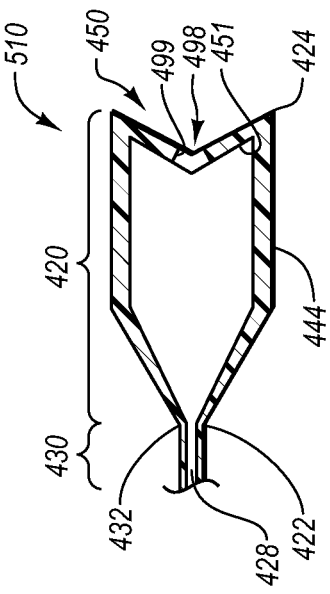
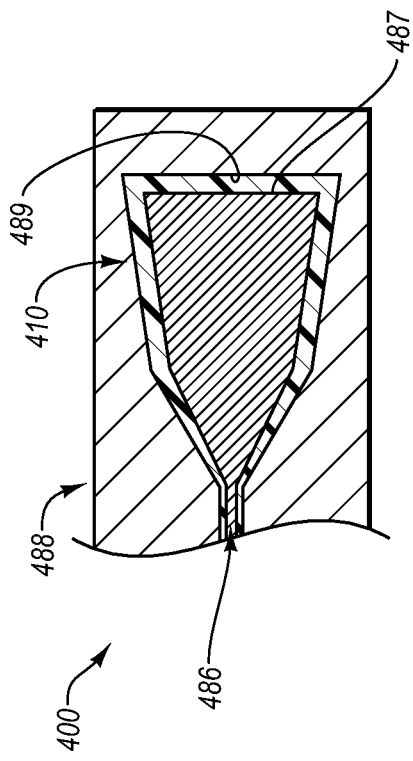
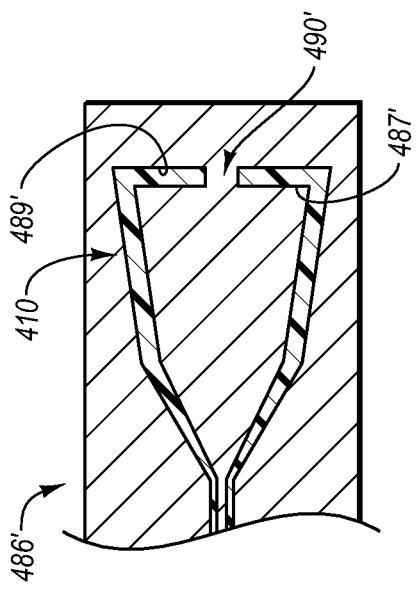

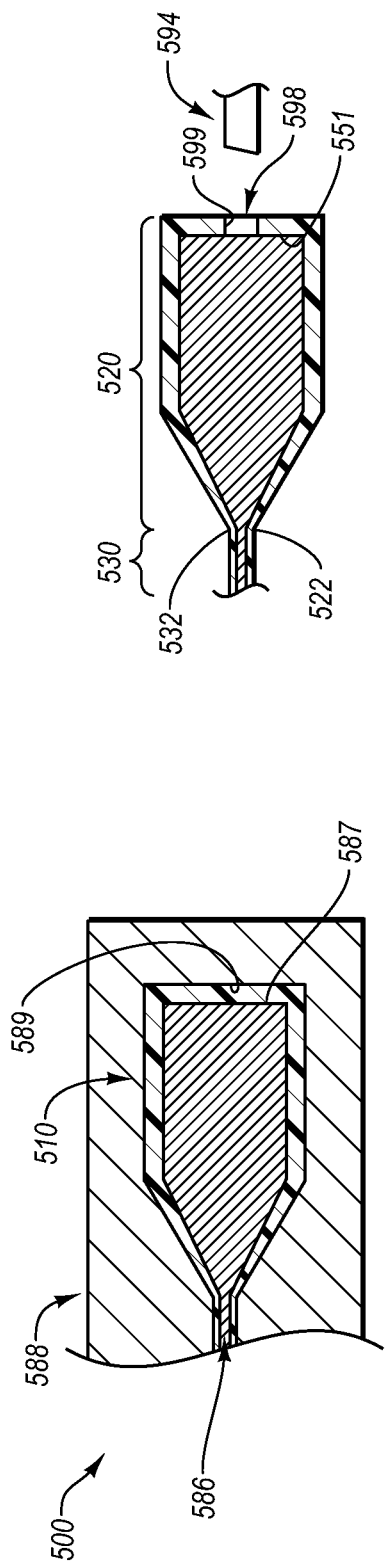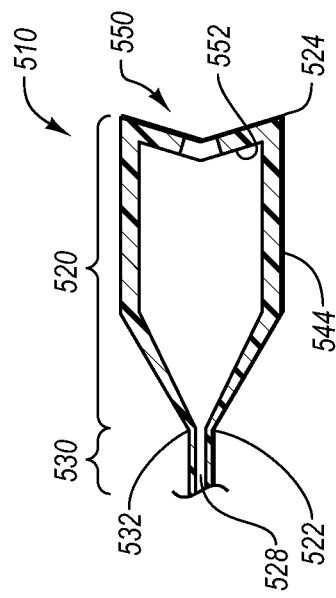
Fig. 6B
Fig. 6C
Fig. 6A

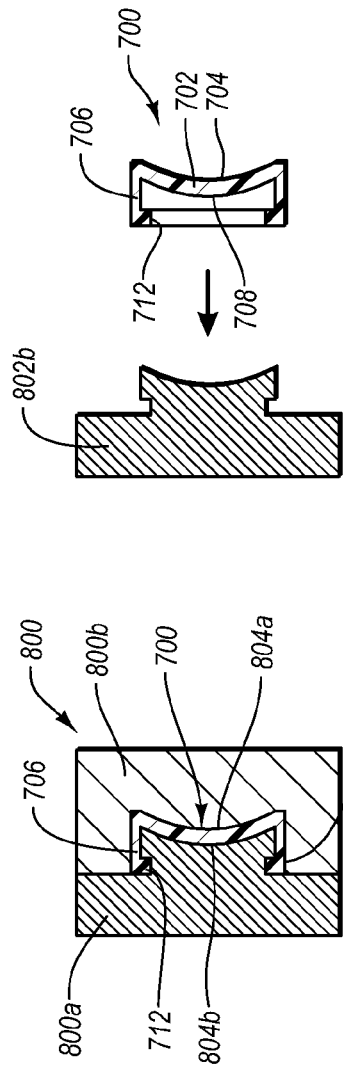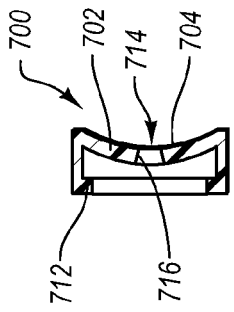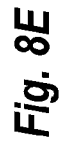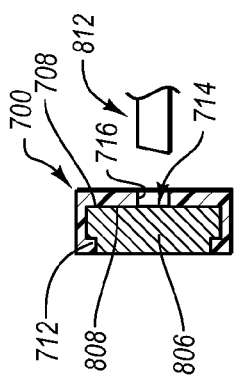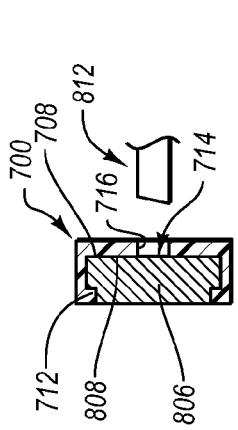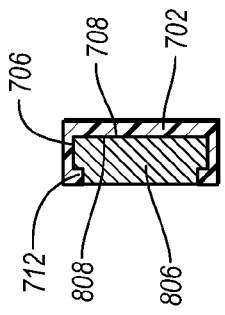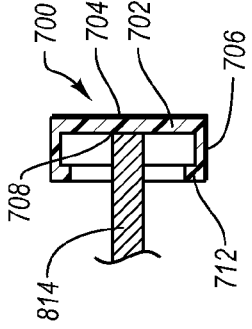

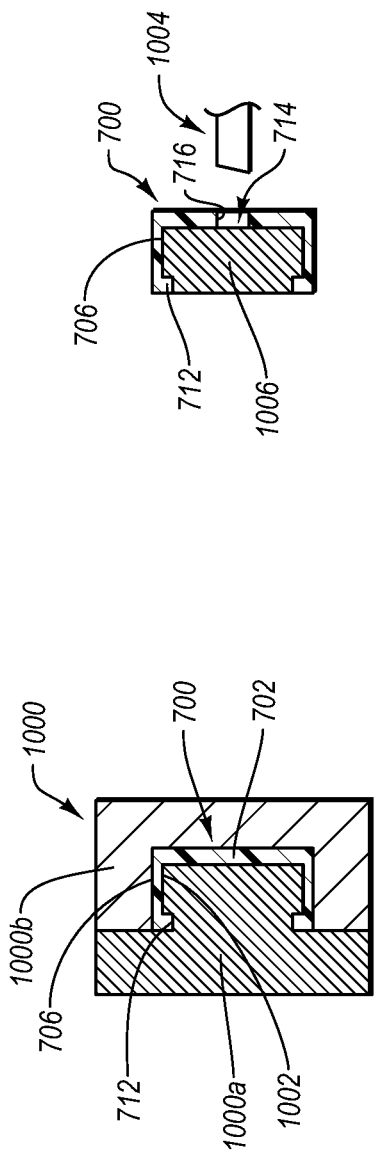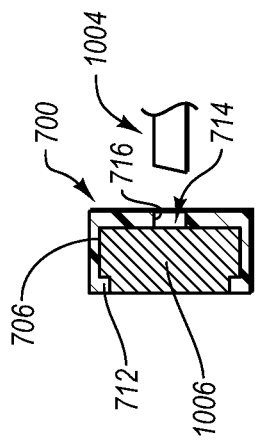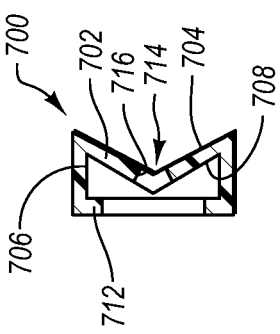

INTRODUCER SHEATH AND METHODS OF MAKING

CROSS-REFERENCE TO RELATED APPLICATIONS

This application is a division of U.S. patent application Ser. No. 12/695,961, entitled "INTRODUCER SHEATH AND METHODS OF MAKING", filed Jan. 28, 2010 which is a continuation-in-part of U.S. patent application Ser. No. 11/427,306, entitled "Introducer Sheath", filed Jun. 28, 2006 and which claims the benefit of U.S. Provisional Patent Application Ser. No. 60/695,602, entitled "Introducer Sheath", filed Jun. 30, 2005, each of the preceding are incorporated herein by reference in its entirety. This application relates to U.S. patent application Ser. No. 11/427,301, entitled "Modular Introducer and Exchange Sheath", and filed Jun. 28, 2006, which claims the benefit of U.S. Provisional Patent Application Ser. No. 60/695,464, entitled "Modular Introducer Sheath", and filed Jun. 30, 2005 and U.S. patent application Ser. No. 11/767,947, filed Jun. 25, 2007, and entitled "Expandable Introducer Sheath to Preserve Guidewire Access", which is a continuation in part of U.S. patent application Ser. No. 11/427,308, filed Jun. 28, 2006, and entitled "Expandable Introducer Sheath", each of the proceeding are incorporated herein by reference in its entirety.

BACKGROUND OF THE INVENTION

1. The Field of the Invention

The present invention relates generally to medical devices and methods. More specifically, embodiments of the invention relate to introducer sheaths and methods of making.

2. The Relevant Technology

A wide variety of sheaths have been developed for use in medical procedures. Sheaths are often used, for example, to access a vessel or artery to allow a surgical procedure to be performed. Sheaths are also used for medical procedures that utilize catheters such as, angioplasty or stenting. In practice, the introducer sheath is generally inserted into the patient's vasculature using the modified Seldinger technique. In the Seldinger technique, a needle is first inserted into the vessel and a guidewire then follows through the needle. Next, the needle is removed and a sheath/dilator combination is advanced over the guidewire. The dilator expands the puncture in the vessel to a size suitable to receive the distal end of an introducer sheath. After the distal end of the sheath is disposed within the vessel, the dilator and guidewire are removed, thereby allowing access to the vessel lumen or other body lumen via the inserted introducer sheath.

Conventionally, introducer sheaths are formed of three or more components that require assembly: a sheath portion, a hub, and a hemostasis valve disposed within the hub. A suitable example of such an assembly is shown in U.S. Pat. No. 5,807,350, which shows an introducer sheath having a construction similar to that described above, the entirety of which is hereby incorporated by reference.

Sheaths such as that described above are generally constructed of multiple pieces that must be assembled to form the sheath. Because the sheath is assembled from separate components, it is often difficult to align the lumen of the distal sheath portion with the lumen of the hub. As a result, additional time must be taken during manufacture to ensure alignment thereby leading to increased costs.

In some instances, the hub at the proximal end of the introducer sheath may be overmolded over the elongated sheath portion. While overmolding may produce a stronger sheath, there is the possibility of damaging a portion of the introducer sheath during the overmolding process. In addition to the cost of the overmolding process, the entire introducer sheath would then have to be discarded. There is a therefore a need for a new introducer sheath having lower manufacturing costs.

BRIEF SUMMARY OF THE INVENTION

These and other limitations may be overcome by embodiments of the present invention, which relates generally to medical devices and methods of use and in particular to introducer sheaths. Embodiments of the invention may provide several designs and methods of manufacture of an improved introducer sheath.

An embodiment of an introducer sheath is described. The introducer sheath includes an elongate tubular portion having a longitudinal axis. The elongate tubular portion is elastically deformable about the longitudinal axis. The introducer sheath includes a hub portion having proximal end and a distal end. The proximal end is substantially wider than the distal end and the distal end secured to the elongate tubular portion. The introducer sheath includes a valved cover elastically secured over the proximal end of the hub portion. The valved cover defines a non-planar outer surface in a relaxed state. The outer surface defines an aperture configured to receive a medical device.

In some embodiments, the hub portion and the elongate tubular portion are formed as a unitary member. The outer surface, in further embodiments, is substantially concave in the relaxed state. In still further embodiments, the aperture includes a sealing surface. The sealing surface, in yet further embodiments, is not generally parallel about a longitudinal axis through the aperture in the relaxed state.

In some embodiments, the sealing surface is configured to form a seal between the medical device and the hub in a deformed state. The aperture, in further embodiments, is tapered. In still further embodiments, the aperture has a diameter that increases with distance from the outer surface.

An embodiment of a method for making an introducer sheath assembly is described. The method includes forming a cap having a top portion and a sidewall portion defining a cavity. The top portion includes a valve secured thereto. A proximal end of a hub portion is inserted into the cavity. The hub portion includes an elongate tubular portion secured to a distal end thereof.

In some embodiments, inserting the proximal end of a hub portion into the cavity comprises elastically deforming the cap. Forming the cap, in further embodiments, includes forming the top portion and sidewall portion and removing a portion of the top portion to form the valve.

An upper surface of the top portion, in some embodiments, has a concave shape. In further embodiments, removing a portion of the top portion to form the valve includes elastically deforming the top portion to decrease a concavity thereof and removing a portion of the elastically deformed top portion to form the valve.

In some embodiments, the valve includes an aperture having a tapered shape when the top portion is in an undeformed state. The aperture, in further embodiments, narrows with distance from the hub portion.

The sidewall portion, in some embodiments, extends from a lower surface of the top portion. Elastically deforming the top portion to decrease a concavity thereof, in further embodiments, includes positioning an urging member within the cavity. In still further embodiments, the urging member comprises a planar upper surface engaging a lower surface of the top portion when the urging member is positioned within the cavity.

In some embodiments, one of an outer surface of the hub portion and an inner surface of the sidewall portion defines a circumferential groove and the other of the outer surface of the hub portion and the inner surface of the sidewall portion includes a circumferential lip. The circumferential groove, in further embodiments, is positioned to receive the circumferential lip when the hub portion is positioned within the cavity. In still further embodiments, the inner surface of the sidewall portion is cylindrical.

An embodiment of an assembly is described. The assembly includes an elongate tubular portion having a longitudinal axis. The elongate tubular portion is elastically deformable about the longitudinal axis. The assembly includes a hub portion having proximal end and a distal end. The proximal end is substantially wider than the distal end and the distal end is secured to the elongate tubular portion. The hub portion and elongate tubular portion define a lumen. The assembly includes a cap having a top portion and a sidewall portion defining a cavity sized to elastically receive a portion of the hub portion. The cap defines a valve in fluid communication with the lumen and is configured to receive a medical device.

In some embodiments, one of an outer surface of the hub portion and an inner surface of the sidewall portion defines a circumferential groove and the other of the outer surface of the hub portion and the inner surface of the sidewall portion comprises a circumferential lip. The circumferential groove, in further embodiments, is positioned to receive the circumferential lip when the hub portion is positioned within the cavity. An upper surface of the top portion, in still further embodiments, has a concave shape and the sidewall portion extends from a lower surface of the top portion.

The sheaths disclosed herein can be used with various medical devices. In one configuration, the sheath can be used in combination with a vessel closure device, such as those shown in U.S. Pat. No. 6,197,042 and pending U.S. patent application Ser. No. 10/638,115 filed Aug. 8, 2003 entitled "Clip Applier and Methods," each of these assigned to a common owner and herein incorporated in their entireties by reference.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims.

BRIEF DESCRIPTION OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIG. 1A is a plan view of an exemplary embodiment of an introducer sheath in accordance with the present invention;

FIG. 1B illustrates a cross-sectional view of the sheath in FIG. 1A and illustrates a valve disposed in the sheath's hub and an alignment member;

FIG. 1C is a cross-sectional view taken along line 1C-1C of the sheath of FIG. 1A in accordance with the present invention;

FIG. 2A illustrates a cross-sectional view of another sheath in accordance with the present invention;

FIG. 2B is cross-sectional view of an alternative embodiment of the sheath of FIG. 2A illustrating the geometric features formed within wall of the sheath in accordance with the present invention;

FIG. 2C is a cross-section view of a portion of an another alternative embodiment of the sheath of FIG. 2A in accordance with the present invention;

FIGS. 4A-4E illustrate cross-sectional views of an embodiment of a sheath in various stages of manufacture in accordance with the present invention;

FIGS. 4C' and 4D' illustrate cross-sectional views of the embodiment of a sheath shown in FIGS. 4A-4E in various stages of manufacture using an alternative embodiment of a forming device in accordance with the present invention;

FIGS. 5A-5C illustrate cross-sectional views of another embodiment of a sheath in various stages of manufacture in accordance with the present invention;

FIG. 5B' illustrates a cross-sectional view of the embodiment of a sheath shown in FIGS. 5A-5C in various stages of manufacture using an alternative embodiment of a forming device in accordance with the present invention;

FIGS. 6A-6C illustrate cross-sectional views of a further embodiment of a sheath in various stages of manufacture in accordance with the present invention;

FIGS. 8A through 8E, including FIGS. 8C' and 8D', illustrate a method for manufacturing a valved cover in accordance with an embodiment of the present invention;

FIGS. 10A through 10C illustrate another alternative method for manufacturing a valved cover in accordance with an embodiment of the present invention.

DETAILED DESCRIPTION

Figure 3A:
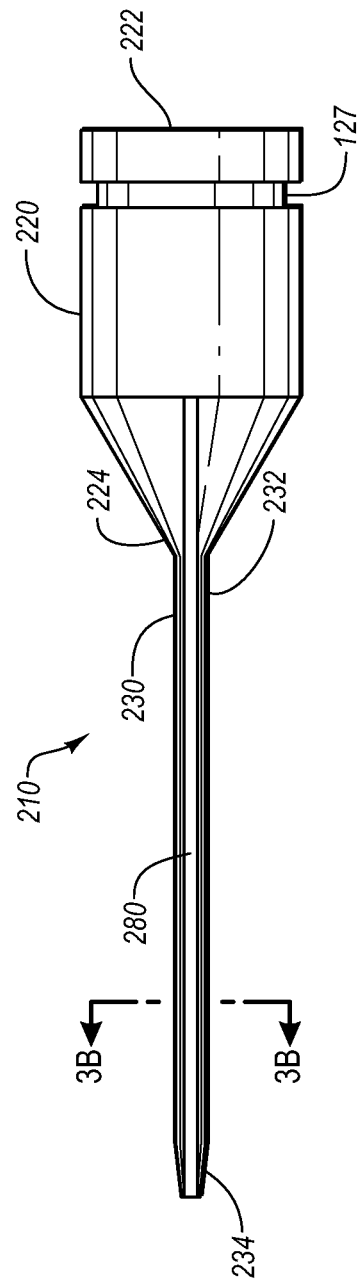
FIG. 3A is a plan view of an alternative embodiment of a sheath in accordance with the present invention.

An introducer sheath in accordance with the present invention is described herein as having portions or members, though it shall be understood that the introducer sheath as described herein may be formed as a unitary member such that the portions or members are portions or members of a unitary device. Embodiments of the introducer sheath are depicted in the drawings, which are not necessarily to scale and are not intended to limit the scope of the invention. It will be understood that the benefits of the present invention are not limited to application with an introducer sheath. Rather, other medical devices may be modified based upon the teaching contained herein such that they to can provide the identified functionality.

The introducer sheath may be formed, by way of example, using a co-extrusion process or an injection molding process or other method that results in a sheath formed as a unitary member. The process by which an introducer sheath is formed may include the use of one or more materials. The materials can be used simultaneously, or at different stages of the manufacturing process.

Typically, the materials used to form the introducer sheath are medical grade synthetics or plastics. Exemplary materials may include, but are not limited to, flexible PVC, polyurethane, silicone, liner low-density polyethylene ("LLDPE"), polyethylene, high density polyethylene, ("DHPE"), polyethylene-lined ethylvinyl acetate ("PE-EVA"), polypropylene, latex, thermoplastic rubber, and the like. In some embodiments, the materials are configured to have chemical resistance, crack resistance, no toxicity, Food and Drug Administration ("FDA") compliance, non-electrically conductive, dimensional stability, and/or be sterilized by ethylene oxide, gamma radiation, autoclave, UV light, ozone, and the like.

In addition, the selection of materials for a particular sheath can depend on a variety of factors that include, but are not limited to, a particular stiffness and/or flexibility of the sheath or any portion of the sheath, including the desired column stiffness and strength to enable insertion of the sheath, a particular shear or split strength for the sheath or any portion of the sheath, the ability to resist kinking, and the like. For example, the material used for the tubular portion of the introducer sheath may be selected based on shear strength or how easily it can be split. Further, certain features of the sheath may be formed to enhance certain characteristics. For example, a strain relief portion may be formed to resist kinking while the elongated tubular portion may be formed to facilitate splitting.

When more than one material is used to form the sheath or to form specific portions of the introducer sheath, the materials may be selected, in addition to the factors identified herein, on a bond strength between the materials or on the elasticity of a particular material. The bond strength, for example, may have an impact on the splitability of the sheath or of a portion of the sheath. The bond strength may also affect the ability of the sheath to expand without splitting.

As described above, the materials of a sheath may be selected based on a splitting or shear property of the materials. One reason for this characteristic or property relates to use of the sheath in medical procedures. For example, when the sheath is used in conjunction with a medical device during a medical procedure, it may be desirable for the introducer sheath to split or shear during insertion or retrieval of the medical device. This may occur, for example, when a vessel is closed with a vessel closure device. The vessel closure device can be used to attach a clip that effectively seals or closes the entry to the body lumen. As the entry or access to the body lumen is closed, the vessel closure device can apply a force that causes the sheath to split. Embodiments of the invention thus contemplate embodiments of the sheath or of portions of the introducer sheath that facilitate splitting at the appropriate time. Further, embodiments of the sheath contemplate structural features that relate to the ease with which a sheath splits without otherwise impacting the use of the sheath.

In accordance with one embodiment of the present invention, an introducer sheath may include a hub member or hub portion having a proximal end and a distal end. The proximal end of the hub portion can be configured to receive a flexible valve member therein. The sheath further includes an elongated tubular portion generally extending from the distal portion of the hub member. The elongated tubular portion is generally centered with an axis of the hub member and the lumen of the tubular portion is aligned with a lumen of the hub portion because the sheath is formed as a single integrated unit in some embodiments. Alternatively, the lumen of the tubular portion can be aligned with a lumen of the hub portion, whether or not axially aligned. The aligning of the lumens can occur during manufacture, such as when the hub portion and the sheath are formed as a single integrated unit.

Referring now to FIG. 1A, there is shown an exemplary embodiment of an introducer sheath 10. The introducer sheath 10 can include a hub portion 20 having a proximal end 22 and a distal end 24, and a tubular portion 30 having a proximal end 32 and a distal end 34. The cross section of the hub portion 20 can be generally cylindrical in nature, although other configurations are contemplated. Exemplary configurations or shapes may include, by way of example, oval, polygonal, elliptical, or other cross-section that can be usable for a medical device that is insertable into a body lumen.

The elongate tubular portion 30 extends from the distal end 24 of the hub portion 20. Because the sheath 10 can be formed as a unitary member, the proximal end 32 of the tubular portion 30 can be integrally formed with the distal end 24 of the hub portion 20. Because the sheath 10 can be formed as a unitary member, the hub portion 20 effectively transitions to the tubular portion 30. Because the transition between the hub portion 20 and the tubular portion 30 may introduce a natural flex point, embodiments of the invention can optionally include a strain relief portion 48, which smoothly transitions the tubular portion 30 of the sheath 10 to the hub portion 20. The strain relief portion 48 can be formed at the transition between the hub portion 20 and the tubular portion 30. More particularly, the strain relief portion 48 can be disposed adjacent the distal end portion of the hub portion 20 and adjacent the proximal end 32 of the elongate tubular portion 30.

The strain relief portion 48 can also be configured to provide additional support to at least the proximal end 32 of the elongate tubular portion 30 to prevent kinking at the transition zone of the proximal end 32 of the elongated portion 30 and the distal end 24 of the hub portion 20. In one embodiment, the strain relief portion 48 can be formed by gradually increasing a thickness of tubular portion 30 as the tubular portion 30 of the sheath 10 transitions to the hub portion 20 of the sheath. Alternatively, the strain relief portion 48 can be formed using other structures or formations that provide, for example, support or kink resistance to the transition from the tubular portion 30 to the hub portion 20. For instance, the strain relief portion 48 can include webs, extensions, or other internal or external structures to increase the strength and/or stiffness of the introducer sheath 10 at the hub portion/tubular portion transition.

With continued reference to FIG. 1A, the distal end 34 of the tubular portion 30 can also include a tapered portion 36 that facilitates entry of the introducer sheath 10, for example, into patient's vasculature or other body lumen. The tapered portion 36 may be formed after the initial forming process of the introducer sheath 10 or be formed as part of the initial forming process. For example, the tapered portion 36 may be formed as part of the extrusion or injection molding processes. Alternatively, the tapered portion 36 may be formed by heat forming, grinding, milling, laser treatment, etching, or other known methods that result in a thinner wall thickness.

FIG. 1B further illustrates a cross-sectional view of the sheath 10 along the line 1B. As shown, a lumen 28 extends from a proximal end 22 of the hub portion 20 to the distal end 34 of the tubular portion 30. The lumen 28 can be generally uniform in cross-section over all or a portion of its length from the proximal end 22 of the hub portion 20 to the distal end 34 of the tubular portion 30. In the illustrated configuration, the lumen 28 has a generally uniform cross-section along its length along the tubular portion 30, while having a generally uniform cross-section portion and a changing cross-section portion along the length of the hub portion 20. It will be understood, however, that other cross-sectional configurations are possible so long as they can accommodate a medical device or instrument inserted therein.

With continued reference to FIG. 1B, the proximal end 22 of the hub portion 20, within the lumen 28 and defined by the inner wall or surface 52 forming the lumen 28, can also include a feature, such as a receiving feature 26, therein, which is configured to receive a flexible valve member 50. The valve member 50 may be inserted after the sheath 10 is formed. For instance, the receiving feature 26, such as a groove or channel, can receive the valve member 50 and retain the same within the hub portion 20. Optionally, a retaining cap (not shown) disposed adjacent to or within the proximal end of the hub portion 20 can aid the receiving feature 26 to retain the flexible valve member 50 within the hub portion 20. Alternatively, the valve member 50 can be integrally formed with the hub portion 20 during the molding process of the sheath 10 and as such the hub portion 20 need not include the receiving feature 26.

The cooperation between the receiving feature 26, optional the retaining cap, and/or the valve member 50 result in a sealed hub portion 20. Stated another way, the valve member 50 is self sealing once it is inserted or formed in the hub portion 20 to prevent fluid escaping from the body lumen.

The valve member 50 can be one of a variety of different seals, including optionally being self-sealing once it is inserted into the hub portion 20. The valve member 50, for example, may have an elastomeric body, such as silicone rubber or other material as described above, with at least one slit and/or other collapsible opening formed therein to allow selective insertion and removal of medical instruments, such as guidewires, catheters, and other such devices. The collapsible openings or other portions of the valve member 50 maintain a fluid tight seal with or against the medical instrument. Thus, blood or other bodily fluids are prevented from leaking out, and unwanted air is prevented from entering into the body. Examples of such flexible membranes or valve members, which can be utilized with the present invention, are shown in U.S. Pat. Nos. 4,798,594, 5,176,652, and 5,453,095 the entireties of which are herein incorporated by reference.

With continued reference to FIG. 1B, illustrated is an optional port member 42 that may be formed on the outer surface or outer wall 44 of the hub portion 20. The port member 42 may function as a fluid port for the sheath 10. Thus, any fluid, such as saline or blood or medication for example, can be added or withdrawn through the port member 42. The port member 42 may also be optionally or alternatively configured to align or position any device or instrument (e.g., a vessel closure device, a catheter) used in conjunction with the sheath 10. The port member 42 may be shaped to interact with an alignment mechanism on a medical device and optionally create a fluid sealed connection. One exemplary type of port member is a member having a luer lock configuration. It will be understood that other types of port can performed the desired function.

Also formed on the outer surface or wall 44 of the hub portion 20 can be a retention recess or ring 46, as shown in FIG. 1A. The recess or ring 46 may be used to secure a cap (not shown) to the sheath 10. The recess or ring 46 can have various configurations to perform the identified and desired function. For instance, although the walls forming the recess or ring 46 are illustrated as being generally parallel, the recess or ring 46 can have tapered wall, curved wall, combinations of generally parallel, tapered, or curved wall, or generally any other configuration that would allow a cap to be secured thereto or for the recess.

It is contemplated that the wall thickness along the length of the elongate tubular portion 30 can be varied to vary mechanical properties of the sheath (e.g., kink resistance, stiffness, flexibility and the like). Further, the thickness of the strain relief 40 (which can vary across the transition between the tubular portion 30 and the hub portion 20), the thickness of the hub portion 20, the diameter of the lumen of the tubular portion 30 and of the lumen of the hub portion 20 can also be varied or specifically selected.

These dimensions of the sheath 10 are often controlled and determined during the manufacturing process. In an injection molding process, for example, the sheath 10 may be formed using a mold. The mold can be machined or configured based on the desired dimensions and configurations of the sheath 10 as described herein. After the mold (which may include more than one part) is formed, the injection molding process can begin by melting a suitable material, such as one described above, and then injecting the melted material into the mold, often under pressure. The mold used in the injection molding process is typically formed such that the molded introducer sheath can be removed after it has cooled and such that the resulting introducer sheath has the desired dimensions and characteristics described herein. As a result, the molded sheath 10 can be a unitary member and may not be assembled from separately formed parts.

Benefits of forming the introducer sheath 10 as a unitary member may include reduced costs, more accurate parts (i.e. dimension control) due to lack of assembly, as well as the ability to balance mechanical properties across the entire sheath 10. For example, the thickness of the walls of the hub portion, the tubular portion, the strain relief, the tapered portion, and/or other portions can be controlled and varied as desired.

Referring now to FIG. 1C, there is shown a cross-sectional view of the sheath 10 in accordance with the present invention along the line 1C-1C of FIG. 1A. In particular, FIG. 2 illustrates a cross-sectional view of the elongate tubular portion 30 of the sheath 10. The elongate tubular portion 30 can include an outer wall 60 and an inner wall 62 thereby defining a wall thickness. Additionally, the lumen 28 may extend along the length of the tubular portion 30. The width or diameter of the lumen 28 can vary and may depend on the intended use of the sheath 10. Because the hub portion 20 and the tubular portion 30 are integrally formed, the lumen 28 may be axially aligned along its length. Stated another way, the axis of the portion of the lumen 28 within the tubular portion 30 can be aligned with the axis of the portion of the lumen 28 within the hub portion 20.

Generally, the outer wall, whether defined by the outer wall 60 of the tubular portion 30 or the outer wall 44 of the hub portion 20, defines the outer surface or wall of the sheath 10. Similarly, the inner wall, whether defined by the inner wall 62 of the tubular portion 30 or the inner wall 52 of the hub portion 20, defines the inner surface or wall and lumen 28 of the sheath 10.

As mentioned above, although the cross-sectional view of the tubular portion 30 is cylindrical in nature, other cross-sectional shapes (polygonal, oval, elliptical, rectangular, etc.) are within the scope of the invention. Further, the lumen 28 may also have an alternative cross-sectional shape other than circular. In one example, the cross-sectional shape of the tubular portion 30 and/or the lumen 28 can be determined by the mold used in an injection molding process. Further, the cross-sectional configuration of the lumen 28 need not be the same as that of the cross-section configuration of the tubular portion 30 as defined by the outer wall of the tubular portion 30, and more generally the sheath 10.

Referring now to FIG. 2A there is shown an exemplary embodiment of an alternative introducer sheath in accordance with the present invention. Much of the description related to the sheath 10 may also apply to the present embodiment of the sheath 110, and vice versa. The alternative embodiment of the sheath will herein be described as having portions similar to that as described above.

As shown in FIG. 2A, the sheath 110 can include a hub portion 120 having a proximal end 122 and a distal end 124, and a tubular portion 130 having a proximal end 132 and a distal end 134. Extending from the proximal end 122 to the distal end 134 is a lumen 128. Generally, the configuration of the lumen 128 and the inner wall or surface forming the lumen 128 may be different from that described with respect to lumen 28 (FIG. 1B). A portion of the lumen 128 in the hub portion 120, or the inner wall or surface 152 can have a stepped configuration. The stepped configuration can include a first portion 154 having a first inner diameter and a second portion 156 having a second diameter larger than the first diameter. This stepped configuration, or the transition between the first portion 154 and the second portion 156 provides or functions as a stop for an inserted valve member 150.

The valve member 150 can be secure within the lumen 128 through a friction or interference fit with the inner surface or wall 152 of the hub portion 120. Alternatively, or in addition to the friction or interference fit, the valve member 150 can be mounted within the lumen 128 through adhesives, thermal or chemical bond, mechanical coupling, such as, but not limited to, the use of a groove or recess in the inner surface or wall 152, or other technique used to mount two components together. In one configuration, a retaining cap 170, having a lumen 172 that can receive a medical device or instrument to be inserted through the valve member 150 and the lumen 128, can secure the valve member 150. The proximal end 174 of the retaining cap 170 can align with, overlap, or be recessed relative to the proximal end 122 depending upon the particular configuration of the end cap 170.

Also formed on the outer surface or wall 152 of the hub portion 120 can be a retention recess or ring 127, as shown in FIG. 2A. The recess or ring 127 may be used to secure a cap (not shown) to the sheath 10. The recess or ring 127 can have various configurations to perform the identified and desired function. For instance, although the walls forming the recess or ring 46 are illustrated as being generally parallel, the recess or ring 46 can have tapered wall, curved wall, combinations of generally parallel, tapered, or curved wall, or generally any other configuration that would allow a cap to be secured thereto or for the recess.

With reference to FIGS. 2A and 2B, the elongated tubular portion 130 includes an outer surface or wall 160 and an inner surface or wall 162. Formed in the inner wall 162 is at least one longitudinal groove 164, and more generally a geometric pattern of grooves, channels, recesses, or other structures, that can extend along an axis parallel to axis extending through the center of the sheath, and centered within the lumen 128. With one or more longitudinal grooves 164, the longitudinal grooves 164 can be formed in various patterns and orientations to provide different characteristics to the tubular portion 130. It is contemplated that additional styles and types of patterns may be utilized in accordance with the present invention. For example, one or more longitudinal grooves 164 may form a sinusoidal pattern disposed about the inner radius of the elongate tubular portion 130. Alternatively, the one or more longitudinal grooves 164 may be configured to run along a different axis than one parallel to an axis extending along the center of the sheath 10. For example, the one or more longitudinal grooves 164 may be formed as one or more spirals as illustrated in FIG. 2C. The one or more longitudinal grooves 164 may also only extend partially along the length of the elongated portion 130. In another embodiment, the one or more longitudinal grooves 164 may extend beyond the tubular portion 130 and into the hub portion 120 (FIG. 1A). In another example, the one or more longitudinal grooves 164 may not extend into the tapered portion of the tubular portion 130.

Generally, it should be understood that the above described configuration of the at least one groove 164 should be considered exemplary and not limiting in any manner. It is contemplated that additional styles and types of patterns may be utilized in accordance with the present invention. For instance, one configuration of the longitudinal grooves 164 can provide increased column stiffness, while another configuration can provide kink resistance and/or resistance to torsional loads. Further, it should be understood that the inner wall 162 could have patterns or configurations of structures other than grooves to achieve desired configurations. For instance, and not by way of limitation, other dents, extensions, channels, recesses, or other structural formations can be created upon or in the inner wall 162.

The formation of the geometric pattern of the plurality of grooves 164, for example, can be formed by machining a corresponding feature in the mold and subsequently using the mold during compression molding, injection molding, blow molding, rotational molding, and/or molding or fabrication processes. As a result, the geometric pattern can be automatically formed during the manufacturing process and no additional steps or acts are required to form the geometric pattern on the inner wall 162.

Referring now to FIG. 3A there is shown an exemplary embodiment of an alternative introducer sheath in accordance with the present invention. Much of the description related to sheath 10 and sheath 110 may also apply to the embodiment of the sheath 210, and vice versa. The alternative embodiment of the sheath will herein be described as having portions similar to that as described above.

As shown in FIG. 3A, the sheath 210 includes a hub portion 220 having a proximal end 222 and a distal end 224. The sheath 210 further includes a composite elongate tubular portion 230 extending from the distal end 224 of the hub portion 220. In this example, the elongated portion 230 may be generally tubular in construction and may include a proximal end 232 and a distal end 234. As described above, the cross-sectional shape of both the elongated portion 230 and the hub portion 220 can be any shape, such as by way of example, circular, elliptical, square, polygonal, and the like. In this example, however, the tubular portion may be composite and can be formed from more than one material.

The sheath 210 may additionally include a feature formed within the hub portion 220 that may be configured to receive a flexible valve member (such as the valve member 50 in FIG. 1B or valve member 150 in FIG. 2A). The flexible valve member may be integrally formed into the hub portion during the molding process of the sheath 210 or may be held within the hub portion 220 using the techniques or methods described herein. Alternatively, the hub portion 220 of the sheath 210 can be molded to provide the elements needed to hold the valve member in place after insertion. The receiving feature 26 (FIG. 1B) or the stepped configuration illustrated in FIG. 2A are examples of features that can retain the valve member after insertion into the hub portion 220.

Figure 3C:
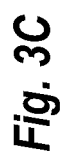
FIG. 3C illustrates a cross-sectional view of an alternative embodiment of a sheath in accordance with the present invention.
Figure 3B:
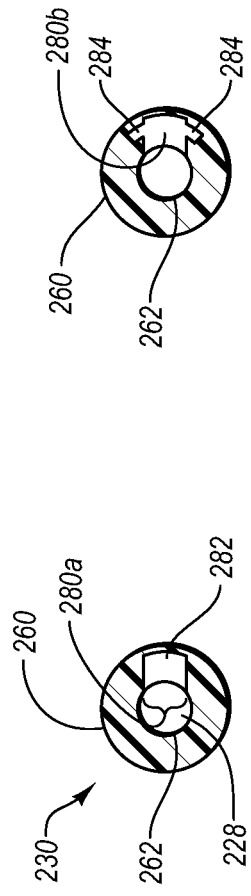
FIG. 3B is a cross-sectional view of the sheath of FIG. 3A taken along line 3A-3A in accordance with the present invention.

Turning now to the tubular portion 230, and with reference to FIGS. 3A and 3B, at least one groove 280 may be disposed within at least a portion of the tubular portion 230, with one being shown in the illustrated configuration. This groove 280 can receive an insert 282 to provide certain characteristics and properties to the tubular portion 230. For instance, the insert 282 can provide structural stiffness or kink resistance to the tubular portion 230 and/or the introducer sheath 210. The groove 280 can extend from (i) the outer surface or wall 260 to the inner surface or wall 262, (ii) the outer surface or wall 260 toward the inner surface or wall 262, or (iii) the inner surface or wall 262 toward the outer surface or wall 260.

As shown in FIGS. 3A and 3B, the groove 280 and/or the insert 282 can extend from the tubular portion 230 to the hub portion 220. Generally, the groove 280 and/or the insert 282 can extend from a portion of the tubular portion 230 to a portion of the hub portion 220. Alternatively, the groove 280 and/or the insert 282 may be formed only in the tubular portion 230, only in the hub portion 220, or in a portion of the hub portion 220 or the tubular portion 230. In other embodiments, one or more grooves 280 and/or inserts 282 can be formed in the sheath 210. Although reference is made to a groove, herein other geometric patterns or configurations of channels, recess, holes, or other structures formed in the sheath can be used. Further, a line or other geometric pattern scored or formed in the sheath, with or without the inclusion of the insert can function in a similar manner to the groove and insert as described herein.

With continued reference to FIGS. 3A and 3B, the insert 282 can be formed in the groove 280 in a variety of manners. In one configuration, the groove 280 can be formed as part of the initial molding process. For instance, the sheath 210 can undergo a first injection molding process where the hub portion 220 and elongated portion 230 are formed as a single unitary unit, with the groove 280 being formed at that time. The mold used to form the sheath 210 may then be adapted, such as by removing the portion of the mold that was responsible for the groove 280, and a second injection molding process may then be performed to inject a second material into the groove 280 to form the insert 282. The insert 282 may effectively bond to the material defining the groove 280 resulting in the sheath, the sheath being a unitary member. One example of a molding technique that can be used to perform the above-described process is an over-molding injection molding process.

It is also contemplated that the first and second injection molding processes can be conducted simultaneously or within a time period of each other, for instance by way of an over-molding injection molding process or a 2-shot injection molding process. In one configuration, a mold can be manufactured and placed into an injection molding machine, wherein the first molding process can form the sheath including the groove 280 shown in FIG. 3A and a second molding process would form the completed sheath by filling the groove 280 with a second material to form the insert 282, resulting in the configuration of FIG. 3B. Thus, the tubular portion 230 can be a composite. The process times can be controlled depending upon the materials to be molded and the desired mechanical properties.

With reference to FIG. 3B, a cross-sectional view of the elongated portion 230 taken about line 3B-3B of FIG. 3A is illustrated. The cross-sectional view of FIG. 3B illustrates the tubular portion 230 after the groove 280 has been formed and filled with a second material, which forms the insert 282. As shown in FIG. 3B, the elongate tubular portion 230 has an outer wall 260 and an inner wall 262 thereby defining a lumen 228 as well as a wall thickness. The insert 282 is shown disposed in groove 280 thereby forming a continuous generally tubular cross-section. In one configuration, the inner wall or surface 262 of the elongated portion 230 typically remains smooth after the second material is injected into the groove 280 to form the insert 282. Alternatively, the inner surface 262 of the elongated portion 230 can have one or more variations, at least one of which can be defined by the insert 282 within the groove 280. For instance, during the process of applying or depositing the second material the mold defining the boundaries for the second material 282 can include the desired pattern of the portion of the inner wall or surface 262 associated with the insert 282.

As previously described above, the second material, as well as the first material, may be chosen based upon desired mechanical properties for the sheath 210. For example, it may be desirable to produce an elongated portion 230 that is easily splitable along a portion of the interface between the first and second materials or through the second material in response to an adequate applied force. In this case, the bond between the first material and the second material can be adjusted through the manufacturing process. As previously stated, the first and second materials may be selected according to the bond between the first material and the second material and on the splitability of the first and/or second materials. For example, the thickness of the first material at the interface with the second material can be less than the thickness of the first material at other locations. This, combined with a second material that fills the groove 280 to form the insert 282 and may have less strength than the first material, may provide a sheath that has particular properties. For example, the tubular portion 230 may be more likely to split along the groove 280 or along any other geometric pattern formed on the inner wall of the tubular portion 230, whether or not filled with a second material or the insert 282. In instances where the geometric pattern such as the groove 280 is filled with a second material to form the insert 282, a bond may be formed automatically during the molding process. Alternatively, thermal bonding, chemical bonding, or other known techniques can be used to facilitate bonding between the similar or dissimilar medical grade materials forming the insert 282 and the remainder of the sheath 210.

As illustrated above, mechanical properties of the tubular portion may be adjusted by forming the elongate tubular portion 230 as a composite member. For example, if it is desirable to produce a sheath that is splitable during use, the second material and the insert 282 may be weaker than the first material, thereby forming a joint wherein the sheath may be easily split by an applied force. Alternatively, the second material or insert 282 can be utilized to stiffen or weaken the overall tubular portion 230. This can be used to prevent kinking, and the like. Alternatively, the second material or insert 282 can be used to stiffen or weaken the overall tubular portion 230 and assist in splitting the sheath during use. For example, the second material or insert 282 may provide stiffness and cause the tubular portion 230 to split at the groove or other geometric pattern in response to an applied force, such as the withdrawal of a medical device like a vessel closure device.

Although the alternative embodiment has been described with respect to specific geometries as well as construction methods this should not be considered limiting in any manner. For example, it is contemplated that the groove 280 may be formed having many different geometric shapes and patterns as well as lengths. Additionally, the groove may include a geometric feature formed along the length thereof, wherein the second material or insert 282 would fill into this feature, thereby interlocking the two materials together.

FIG. 3C, for example, illustrates another configuration of the interface between a first material and a second material or between the groove and an insert. In particular, the groove 280 includes sub-grooves 284 that extend outwardly from the main portion of the groove 280. These sub-grooves 284 can receive or be filled with the second material that forms the insert 282 during the injection molding process and provide a mechanical connection or coupling between the two materials and between the groove 280 and the insert 282. As such, the sub-grooves 284, together with the insert 282 or second material deposited therein, may function as interlocking features that may mechanically tie the portions of the tubular portion 230 together. By so doing, the two portions of the tubular portion 230 can be mounted or coupled together through both the bonding of the two materials and the mechanical coupling of the interlocking features formed in the groove 280 and the insert 282.

It will be understood that in another configuration, the insert 282 can be formed separately from the remainder of the sheath 210. The insert 282 can then be mounted or coupled to the groove 280 during subsequent processing. For instance, the insert 282 can be mounted or coupled to the groove 280 using adhesives, thermal or chemical bonding, and/or other techniques to mount or couple similar or dissimilar medical grade materials. Further, the insert 282 can mount or couple using mechanical structures, such as but not limited to, the interlocking features, with or without the use of adhesives, thermal or chemical bonding, and/or other techniques to mount or couple similar or dissimilar medical grade materials.

Because the sheath can be formed by an injection molding process using molten or melted material, the shape of the sub-grooves 284, or other mechanical structures that) facilitate mechanical coupling between two components, can vary and accommodate any desired purpose. In some instances, the formation or filling of the groove 280 with the second material to form the insert 282 may cause the first material to melt, thereby causing the two materials to bond. For example, the shape of the feature 284 may include extensions that prevent the first material from separating from the second material without tearing or shearing. This can strengthen the bond, in one example, between the first and second materials. Further, the interlocking feature may ensure that the tubular portion shears at the groove 280 owing to the strength or lack thereof of the second material.

The at least one interlocking features illustrated in FIG. 3C can extend from a proximal end 232 to a distal end 234 of the tubular portion 230 and/or the introducer sheath 210. It will be understood, however, that the at least one interlocking feature can extend only part way from the distal end toward the proximal end, from the proximal end to the distal end, or at any location along the length of the tubular portion 130 and/or the sheath 210.

In addition to the use of a second material to fill the groove 280 or other geometric pattern, it is further contemplated that more than two materials may be utilized to form the introducer sheath in accordance with the present invention or that other portions of the sheath may be formed from a second material. For example, a first material may be utilized to form the hub portion and one or more materials (which may include the first material) may be utilized to form the elongated portion of the sheath. Again, the selection of materials may depend on the end use of the sheath, properties of medical devices used with the sheath, and the like or any combination thereof. Although the present invention has been shown and described in accordance with specific embodiments these should not be considered limiting in any manner. For example, multiple materials may be utilized to form a unitary sheath in accordance with the present invention, wherein multiple injection molding processes are performed simultaneously or in stages to form the unitary sheath in accordance with the present invention.

Referring generally to FIGS. 4A-4E, there is shown a system 300 for manufacturing a sheath 310 during various stages of manufacture. The introducer sheath 310 of this embodiment may be at least partially functionally similar to that of the introducer sheaths, 10, 110, 210 previously described above and shown in FIGS. 1A-3C in most respects, wherein certain features will not be described in relation to this embodiment wherein those components may function in the manner as described above and are hereby incorporated into this alternative embodiment described below. Like structures and/or components are given like reference numerals.

The introducer sheath 310 may include a hub portion 320, which includes a proximal end 322 and a distal end 324, and/or a tubular portion 330, which includes a proximal end 332 and a distal end (not shown). The cross section of the hub portion 320 can be generally cylindrical in nature, although other configurations are contemplated. The hub portion 320 may include a valve portion 350. As shown in FIG. 4A, the valve portion 350 may be a portion of a surface on the distal end 324 of the hub portion 320. The valve portion 350 may include a distal surface 351.

Although not illustrated in FIGS. 4A-4E, the sheath 310 may include an optional port member, such as the optional port member 42 shown in FIG. 1B, that may be formed on the outer surface or outer wall 344 of the hub portion 320. The sheath 310 may further include a retention recess or ring, such as the retention recess or ring 46 shown in FIG. 1A.

Referring specifically to FIG. 4A, the system 300 for manufacturing a sheath 310 may include a first forming device 386 and/or an external forming device 388. The first forming device 386 may include a concave proximal end 387. The external forming device 388 may include a convex distal end 389. For instance, the proximal end 387 of the first forming device 386 and/or the distal end 389 of the external forming device 388 may be curved, as shown in FIG. 4A, or may come in other convex shapes such as an inverted "V" shape and/or other shapes that are substantially non-parallel toward the distal end 324 of the hub portion 320.

In an injection molding process, for example, the sheath 310 may be formed using core pin as the first forming device 386 and a mold as the external forming device 388. The first forming device 386 and/or the external forming device 388 can be machined or configured based on the desired dimensions and configurations of the sheath 310 as described herein.

After the first forming device 386 and/or the external forming device 388, which may include multiple parts, are formed (i.e. milled, lathed, etc.), the injection molding process may begin by melting a suitable material, such as one described above, and then injecting the melted material using the first forming device 386 and/or the external forming device 388, often under pressure. The external forming device 388 may be formed such that the molded introducer sheath 310 can be removed after it has cooled and such that the resulting introducer sheath 310 has the desired dimensions and characteristics described herein. As a result, the molded sheath 310 can be a unitary member and may not require assembly from separately formed parts.

As shown in FIG. 4A, the valve portion 350 may be formed in a concave shape. As shown in FIG. 4B, the valve portion 350 may have a concave shape in a relaxed state after the sheath 310 is formed and the first forming device 386 and/or the external forming device 388 are removed. The first forming device 386 may be removed through the lumen 328. For example, the sheath 310 may be sufficiently elastic to allow the first forming device 386 to be removed through the lumen 328.

A second forming device 392 may be inserted into the hub portion 320, as shown in FIG. 4C. The second forming device 392 may be inserted through the tubular portion 330. The second forming device 392 may include a proximal end 393 that is substantially planar. The second forming device 392 may deform the valve portion 350 from the concave shape in the relaxed state, as shown in FIG. 4B, toward a substantially planar shape in a deformed state, as shown in FIG. 4C. For example, the proximal end 393 of the second forming device 392 may abut at least a portion of the distal surface 351 of the valve member 350 to deform the valve member 350. In other embodiments, the proximal end 393 of the second forming device 392 may vary in shape. For instance, the proximal end 393 may be convex, square, and/or otherwise shaped. The proximal end 393 of the second forming device 392 may have a surface area that is substantially the same size as the distal surface 351 of the valve portion 350, as shown in FIG. 4C.

As shown in FIG. 4C', an alternative embodiment of a second forming device 392' may be inserted into the hub portion 320. The second forming device 392' may be inserted through the tubular portion 330. The second forming device 392' may deform the valve portion 350 from the concave shape in the relaxed state, as shown in FIG. 4B, toward a substantially planar shape in a deformed state, as shown in FIG. 4C'. The proximal end 393' of the second forming device 392' may have a surface area that is substantially smaller than the distal surface 351 of the valve portion 350. For example, the proximal end 393' of the second forming device 392' may have a surface area that is approximately the same size as the aperture 398 to be formed. In another example, the proximal end of the second forming device 392' may have a surface area that is approximately the same size as an area of the lumen 328 of the tubular portion 330. As shown in FIG. 4D', a blade 394 may have a dimension that is approximately the same as a dimension of the second forming device 392'. Other sizes and/or shapes of the second forming device 392' may be used.

As shown in FIG. 4D, an aperture 398 may be formed. The aperture 398 may be formed while the valve portion 350 is in the deformed state. Typically, the aperture 398 may be formed after the sheath 310 has cooled. However, it may be desirable to form the aperture 398 before and/or during the cooling process.

The aperture 398 may be formed using a blade 394. The blade 394 may include a twist drill bit, a boring bit, and/or other blades. The blade 394 may remove material through at least a portion of the distal surface 351 of the valve portion 350. The blade 394 may contact the second forming device 392 during forming of the aperture 398.

The blade 394 may have a hardness that is lower than the hardness of the second forming device 392 and/or higher than the hardness of the valve portion 350. Having a hardness that is lower than the second forming device 392 may limit damage to the second forming device 392. However, other hardnesses may be selected for the blade 394, the second forming device 392, and/or the valve portion 350.

The blade 394 may form a substantially cylindrical aperture 398. Alternatively, the blade 394 may produce other shapes of apertures 398. Typically, the aperture 398 may be formed through a central portion of the distal surface 351 of the valve portion 350. For example, a longitudinal axis of the aperture 398 may be aligned with a longitudinal axis of the hub portion 320 and/or tubular portion 330.

The aperture 398 of the valve portion 350 may provide a sealed hub portion 320. Stated another way, the aperture 398 of the valve portion 350 may be self-sealing to prevent fluid escaping from the body lumen. To facilitate sealing, the aperture 398 may include a sealing surface 399. The sealing surface 399 may be configured to form a seal between a medical device and the hub portion 320. The sealing surface 399, in the deformed state, may be generally parallel to the longitudinal axis of the hub portion 320 and/or tubular portion 330 (i.e. the sealing surface 399 may be substantially cylindrical).

As shown in FIG. 4E, the valve portion 350 may still be generally concave in the relaxed state after the aperture 398 is formed. The sealing surface 399, in the relaxed state, may be generally nonparallel to the longitudinal axis of the hub portion 320 and/or tubular portion 330 (i.e. the sealing surface 399 may be substantially conic).

When in use, a medical device may be inserted through the aperture 398 while the valve portion 350 is in the relaxed state. An outer surface of the medical device may contact at least a portion of the sealing surface 399 (i.e. a proximal edge and/or other portion). When the medical device has been inserted approximately a desired distance, the medical device may be retracted. Retracting the medical device may transition the valve portion 350 from the relaxed state toward the deformed state. For example, the outer surface of the medical device may engage the sealing surface 399 such that the valve portion 350 may transition toward the deformed state.

Benefits of forming an aperture 398 in the hub portion 320 of introducer sheath 310 may include reduced costs (i.e. assembly costs for a separate flexible valve member), more accurate parts (i.e. dimension control) due to lack of assembly, as well as the ability to balance mechanical properties across the entire sheath 310.

Referring generally to FIGS. 5A-5C, there is shown a system 400 for manufacturing a sheath 410 during various stages of manufacture. The introducer sheath 410 of this alternative embodiment may be at least partially functionally similar to that of the introducer sheaths, 10, 110, 210, 310 previously described above and shown in FIGS. 1A-4E in most respects, wherein certain features will not be described in relation to this embodiment wherein those components may function in the manner as described above and are hereby incorporated into this alternative embodiment described below.

For example, although not illustrated in FIGS. 5A-5C, the sheath 410 may include an optional port member, such as the optional port member 42 shown in FIG. 1B, that may be formed on the outer surface or outer wall 444 of the hub portion 420. In another example, the sheath 410 may further include a retention recess or ring, such as the retention recess or ring 46 shown in FIG. 1A. Like structures and/or components are given like reference numerals.

The introducer sheath 410 may include a hub portion 420, which includes a proximal end 422 and a distal end 424, and/or a tubular portion 430, which includes a proximal end 432 and a distal end 434. The cross section of the hub portion 420 can be generally cylindrical in nature, although other configurations are contemplated. The hub portion 420 may include a valve portion 450. As shown in FIG. 5A, the valve portion 450 may be a portion of a surface on the distal end 424 of the hub portion 420. The valve portion 450 may include a distal surface 451.

Referring specifically to FIG. 5A, the system 400 for manufacturing a sheath 410 may include a forming device 486 and/or an external forming device 488. The forming device 486 may include a substantially planar proximal end 487. The forming device 486 may further be flared toward the proximal end 487. The external forming device 488 may include a substantially planar distal end 489. The external forming device 488 may further be flared internally toward the distal end 489. In an injection molding process, for example, the sheath 410 may be formed using core pin as the forming device 486 and a mold as the external forming device 488. The forming device 486 and/or the external forming device 488 can be machined or configured based on the desired dimensions and configurations of the sheath 410 as described herein.

After the forming device 486 and/or the external forming device 488, which may include multiple parts, are formed (i.e. milled, lathed, etc.), the injection molding process may begin by melting a suitable material, such as one described above, and then injecting the melted material using the forming device 486 and/or the external forming device 488, often under pressure.

As shown in FIG. 5A, the valve portion 450 may be formed in a substantially planar shape. The sheath 410 may be formed in a deformed rather than a relaxed state. For example, the geometry of the forming device 486 and/or external forming device 488 may determine whether the sheath 410 is formed in a relaxed or a deformed state. In the present example, the sheath 410 may be formed in a deformed state because the forming device 486 and/or external forming device 488 are flared toward their proximal end 487 and/or distal end 489, respectively. The flaring may generate internal stresses within the sheath 410 to deflect the valve portion 450 toward a substantially concave shape in a relaxed state.

As shown in FIG. 5B, an aperture 498 may be formed. The aperture 498 may be formed while the valve portion 450 is in the deformed state. The aperture 498 may be formed using a blade 494 that may remove material through at least a portion of the distal surface 451 of the valve portion 450. The blade 494 may contact the forming device 486 during forming of the aperture 498. The blade 494 may have a hardness that is lower than the hardness of the forming device 486 and/or higher than the hardness of the valve portion 450.

The blade 494 may form a substantially cylindrical aperture 498. Alternatively, the blade 494 may produce other shapes of apertures 498. Typically, the aperture 498 may be formed through a central portion of the distal surface 451 of the valve portion 450. For example, a longitudinal axis of the aperture 498 may be aligned with a longitudinal axis of the hub portion 420 and/or tubular portion 430.

The aperture 498 of the valve portion 450 may provide a sealed hub portion 420. Stated another way, the aperture 498 of the valve portion 450 may be self-sealing to prevent fluid escaping from the body lumen. To facilitate sealing, the aperture 498 may include a sealing surface 499. The sealing surface 499 may be configured to form a seal between a medical device and the hub portion 420. The sealing surface 499, in the deformed state, may be generally parallel to the longitudinal axis of the hub portion 420 and/or tubular portion 430 (i.e. the sealing surface 499 may be substantially cylindrical).

As shown in FIG. 5B', an alternative embodiment of a forming device 486' may be used to form the sheath 410. The forming device 486' may be a combination of the forming device 486 and external forming device 488 of the embodiment shown in FIG. 5A. However, in this alternative embodiment, an aperture forming member 490' may be added to the forming device 486' to form the aperture 498 in the valve portion 450 of the sheath 410. The aperture forming member 490' may eliminate the need for a blade 494 to form the aperture 498.

An aperture forming member 490' may be used in other embodiments. For example, an aperture forming member 490' may be used with the system 400 for manufacturing a sheath 410. In the system 400, the aperture forming member 490' may be shaped to generally match the shape of the aperture 498 in the relaxed shape. The use of an aperture forming member 490' in the system 300 may eliminate the need for a second forming device 392 and/or a blade 394.

In the present example, the aperture forming member 490' may be substantially cylindrically shaped to form a substantially cylindrical shaped aperture 498. However, other shapes may be used.

As shown in FIG. 5C, the valve portion 450 may still be generally concave in the relaxed state after the aperture 498 is formed (i.e. by the blade 494 or by the aperture forming member 490'). The sealing surface 499, in the relaxed state, may be generally nonparallel to the longitudinal axis of the hub portion 420 and/or tubular portion 430 (i.e. the sealing surface 499 may be substantially conic). The valve portion 450 may have a concave shape in a relaxed state after the sheath 410 is formed and the forming device 486 and/or the external forming device 488 or the forming device 486' with an aperture forming member 490 are removed.

Referring generally to FIGS. 6A-6C, there is shown a system 500 for manufacturing a sheath 510 during various stages of manufacture. The introducer sheath 510 of this alternative embodiment may be at least partially functionally similar to that of the introducer sheaths, 10, 110, 210, 310 previously described above and shown in FIGS. 1A-5C in most respects, wherein certain features will not be described in relation to this embodiment wherein those components may function in the manner as described above and are hereby incorporated into this alternative embodiment described below.

For example, although not illustrated in FIGS. 6A-6C, the sheath 510 may include an optional port member, such as the optional port member 42 shown in FIG. 1B, that may be formed on the outer surface or outer wall 544 of the hub portion 520. In another example, the sheath 510 may further include a retention recess or ring, such as the retention recess or ring 46 shown in FIG. 1A. Like structures and/or components are given like reference numerals.

The introducer sheath 510 may include a hub portion 520, which includes a proximal end 522 and a distal end 524, and/or a tubular portion 530, which includes a proximal end 532 and a distal end 534. The cross section of the hub portion 520 can be generally cylindrical in nature, although other configurations are contemplated. The hub portion 520 may include a valve portion 550. As shown in FIG. 6A, the valve portion 550 may be a portion of a surface on the distal end 524 of the hub portion 520. The valve portion 550 may include a distal surface 551.

Referring specifically to FIG. 6A, the system 500 for manufacturing a sheath 510 may include a forming device 586 and/or an external forming device 588. The forming device 586 may include a substantially planar proximal end 587. The forming device 586 may further include a substantially cylindrical shape toward the proximal end 587. The external forming device 588 may include a substantially planar distal end 589. The external forming device 588 may further include a substantially cylindrical internal shape toward the distal end 589. In an injection molding process, for example, the sheath 510 may be formed using core pin as the forming device 586 and a mold as the external forming device 588. The forming device 586 and/or the external forming device 588 can be machined or configured based on the desired dimensions and configurations of the sheath 510 as described herein.

After the forming device 586 and/or the external forming device 588, which may include multiple parts, are formed (i.e. milled, lathed, etc.), the injection molding process may begin by melting a suitable material, such as one described above, and then injecting the melted material using the forming device 586 and/or the external forming device 588, often under pressure.

As shown in FIG. 6A, the valve portion 550 may be formed in a substantially planar shape. Because the forming device 586, in the present example, may be unflared (i.e. substantially cylindrical) toward the proximal end 587 and/or have a substantially planar proximal end 587, the valve portion 550 may remain substantially planar in the relaxed state. A manufacturing process may be used to facilitate transitioning the valve portion 550 toward a substantially concave shape in the relaxed state. In one example, an interim stress differential may be created in and/or around the valve portion 550. The interim stress differential may be created before the formed sheath 510 has substantially cooled. The interim stress differential may be created by, for example the temperatures of the molds near the valve portion 550, the thickness along the valve portion 550, other aspects of the mold and/or valve portion may be varied, or combinations thereof.

As shown in FIG. 6B, an aperture 598 may be formed. The aperture 598 may be formed before, during, or after a manufacturing processes is used to facilitate transitioning the valve portion 550 toward a substantially concave shape in the relaxed state. The aperture 598 may be formed using a blade 594 that may remove material through at least a portion of the distal surface 551 of the valve portion 550. The blade 594 may contact the forming device 586 during forming of the aperture 598.

The blade 594 may form a substantially cylindrical aperture 598. Alternatively, the blade 594 may produce other shapes of apertures 598.

The aperture 598 of the valve portion 550 may provide a sealed hub portion 520. Stated another way, the aperture 598 of the valve portion 550 may be self sealing to prevent fluid escaping from the body lumen. To facilitate sealing, the aperture 598 may include a sealing surface 599. The sealing surface 599 may be configured to form a seal between a medical device and the hub portion 520. The sealing surface 599, in the deformed state, may be generally parallel to the longitudinal axis of the hub portion 520 and/or tubular portion 530 (i.e. the sealing surface 599 may be substantially cylindrical).

An alternative embodiment of a forming device (not shown), similar to the forming device shown in FIG. 5B' may be used to form the sheath 510. The forming device may be a combination of the forming device 586 and external forming device 588 of the embodiment shown in FIG. 6A. For example, the forming device may include a substantially planar exterior proximal end and/or interior distal end, similar to the forming device 486' shown in FIG. 5B'. The forming device may further include a substantially cylindrical shape toward the exterior proximal end and/or the interior distal end rather than being flared toward the exterior proximal end 487 and/or interior distal end 489 of the forming device 486' shown in FIG. 5B'.

As shown in FIG. 6C, the valve portion 550 may still be generally concave in the relaxed state after the aperture 598 is formed (i.e. by the blade 594 or by an aperture forming member).

Although the present examples describe manufacturing the sheaths 310, 410, 510 as unitary members, the hub portions 320, 420, 520 may be manufactured separately from the tubular portions 330, 430, 530. For example, the hub portion 320, 420, 520 may be manufactured separately as generally described above and then joined with a tubular portion 330, 430, 530. Furthermore, although the present example describes an injection molding process, other forming processes may be used to from the hub portion 320, 420, 520 and/or tubular portion 330, 430, 530. For instance, it is contemplated that a lost wax process and/or other suitable process may be used to form the tubular portion 330, 430, 530 and/or hub portion 320, 420, 520 having a substantially concave valve portion 350, 450, 550 in a relaxed state.

Figure 7A:
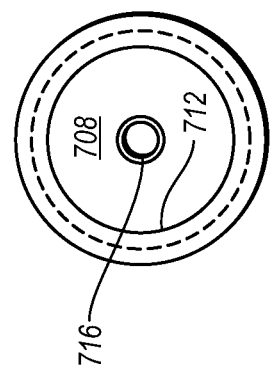
FIGS. 7A-7C illustrate a valved cover suitable for use with a sheath in accordance with an embodiment of the present invention.
Figure 7B:
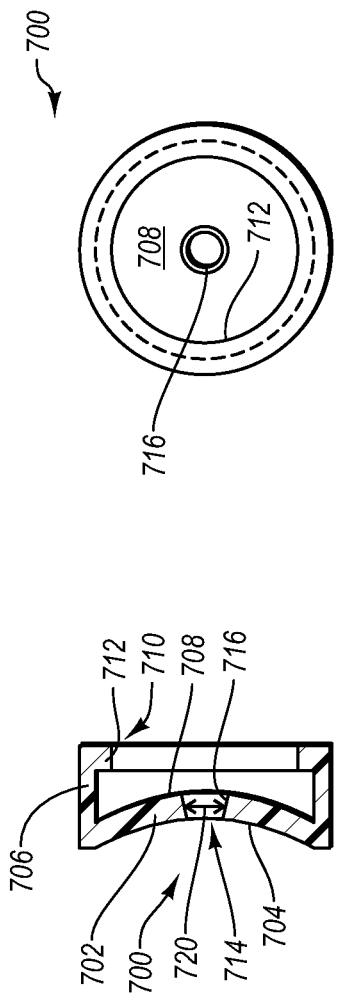
Figure 7C:
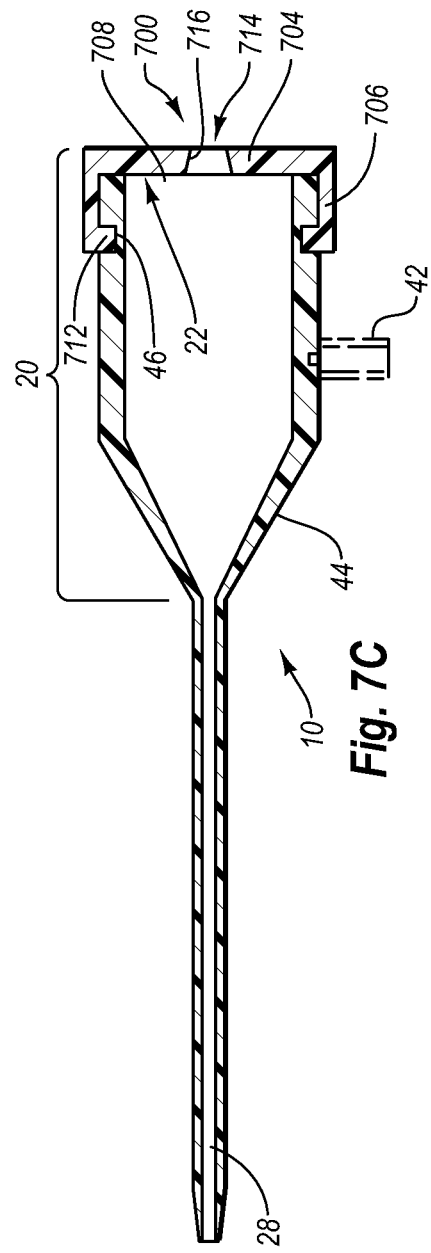

Referring to FIGS. 7A through 7C, in an alternative embodiment an introducer sheath, such as is illustrated in FIGS. 1A through 3C may be adapted to receive a valved cover 700. The cover 700 may be sized, for example to cover a portion of the hub 20 proximate the proximal end 22 of the introducer sheath of FIGS. 1A through 1C. The cover 700 may likewise be positioned over a portion of the proximal end 122 of the hub 120 of FIGS. 2A through 2C or the proximal end 222 of the hub 220 of the introducer sheath of FIGS. 3A through 3C. In embodiments where the valved cover 700 is used the flexible valve member 50 and corresponding receiving feature 26 may be omitted. Alternatively, one or both of the valve member 50 and receiving feature 26 may be retained in order to provide a redundant seal or to provide the option of positioning a seal member 50 in the receiving feature 26 if desired. Likewise, with respect to FIGS. 2A through 2C, the seal member 150 may be omitted or retained where a valved cover 700 is used.

Referring specifically to FIGS. 7A and 7B, the valved cover 700 may include an upper portion sized to cover the proximal end 22, 122, 222 of the hub portion 20, 120, 220. The upper portion 702 may include an outer surface 704 that is exposed when the valved cover 700 is secured to the hub portion 20, 120, 220. The outer surface 704 preferably has an inverted or concave shape. For example, the outer surface 704 may have a spherical or conical shape. A sidewall portion 706 may secure to the upper portion 702. For example, the sidewall portion 706 may extend around a perimeter of the upper portion 702 such that the upper portion and sidewall portion 706 define a cavity sized to receive the proximal end 22, 122, 222 of the hub portion 20, 120, 220. Alternatively, the cavity may be sized to receive the proximal end 22, 122, 222 of the hub portion 20, 120, 220 only after elastic deformation thereof. In the illustrated embodiment, the sidewall portion 706 defines a cylindrical inner surface 710. However, the inner surface 710 may be shaped to conform to whatever shape is had near the proximal end 22, 122, 222 of the hub portion 20, 120, 220.

A retaining member 712 may project inwardly from the inner surface 710 and engage the hub portion 20, 120, 220 to resist removal thereof. In the illustrated embodiment, the retaining member 712 is embodied as a lip extending circumferentially around the inner surface 710. The lip or retaining member 712 may be sized to fit within the retention recess, or ring, 46 in the embodiments of FIGS. 1A through 1C or within the retention recess, or ring, 127 in the embodiments of FIGS. 2A through 3C. In an alternative embodiment, the lip or retaining member 712 may be replaced by a circumferential groove formed in the inner surface 810 of the sidewall 706 and sized to receive a ridge extending circumferentially around the hub portion 20, 120, 220 near the proximal end 22, 122, 222.

The valve cover 700 may be formed of an elastic material, such as an elastic, biocompatible polymer. The sidewall 706 and retaining member 712 preferably deforms sufficiently to allow the retaining member 712 to be passed over the proximal end 22, 122, 222 of the hub portion 20, 120, 220 and into engagement with the retention recess, or ring, 46.

A valve 714 may be formed in the top portion 702. The valve 714 may be sized to receive a catheter or other slender instrument for threading through the introducer sheath into the vasculature of a patient. In the illustrated embodiment, the valve 714 is embodied as an aperture 716 extending through the top portion 702. Alternatively, the valve 714 may be a valving structure secured within the aperture 716 such as by means of overmolding, adhesive, or the like. The aperture 716 may be tapered when the top portion 702 is not deformed by an external force, such as an aperture 716 having a conical shape. The aperture 716 may be tapered such that the diameter 720 of the aperture 716 increases with distance from the upper surface 704 of the top portion.

Referring to FIGS. 8A through 8E, the valve 700 may be formed in the top portion 702 according to the method illustrated. As shown in FIG. 8A, the sidewall 706 and top portion 702 may be formed, such as by a molding process. As is apparent in FIG. 8A, the mold 800 includes mold portions 800a, 800b combinable to form a cavity 802 that may be filled with a liquid polymer that becomes solid through a cooling or curing process. The cavity 802 may include surfaces 804a, 804b positioned on either side of the top portion 702 of the molded valved cover 700. The surfaces 804a, 804b may be shaped such that the upper surface 704 has an inverted or concave shape following the molding process as shown by the valved cover 700 shown in FIG. 8B. For example, the surfaces 804a, 804b may have a spherical shape. Alternatively, the surfaces 804a, 804b may have a conical shape such that the upper surface 704 has a conical shape.

Referring to FIG. 8C, the concavity of the upper surface 704 may then be reduced by deforming the top portion 702 prior to forming the valve 714. In the illustrated embodiment, reduction of the concavity of the upper surface 704 is accomplished by inserting a mandrel 806 within the cavity defined by the sidewall 706 and top portion 702. The mandrel 806 may have an upper surface 808 that is flat or has a radius of curvature greater than an undeformed radius of curvature of the lower surface 810 of the top portion 702, such that as the mandrel 806 is urged against the lower surface 810, the concavity of the upper surface 704 is reduced.

Referring to FIG. 8D, the aperture 716 for the valve 714 may then be formed in the top portion 702, such as by means of cutting tool 812, such as a rotating drill, punch, actuated blade, or the like. The mandrel 806 may then be removed to yield a valved cover 700 such as is illustrated in FIGS. 7A and 7B. Referring to FIGS. 8C' and 8D', in some embodiments, the mandrel 806 may be embodied by a rod 814 pressed against the lower surface 808 during the cutting step illustrated in FIG. 8D'. For example, the rod 814 may have an upper surface 814 that is has an area substantially smaller than the area of the lower surface 810 of the top portion 702. For example, the rod 814 may have an area that is slightly greater or smaller (e.g. ±5 to 10%) that of the aperture 716.

Upon removal of the mandrel 806 or rod 814, the top portion 702 may elastically return to its undeformed shape, causing the aperture 716 to become tapered due to the return of the top portion 702 to a concave shape.

Figure 9C:
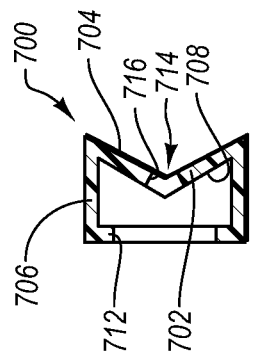
FIGS. 9A through 9C, including FIG. 9B', illustrate an alternative method for manufacturing a valved cover in accordance with an embodiment of the present invention.
Figure 9B:
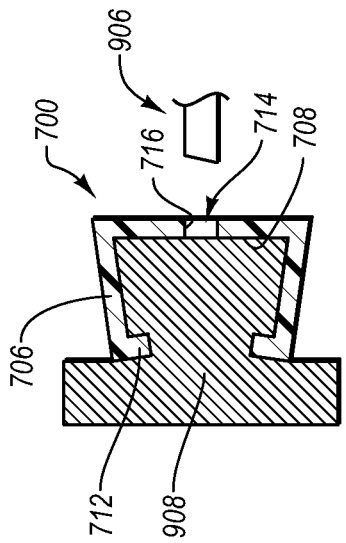
Figure 9A:
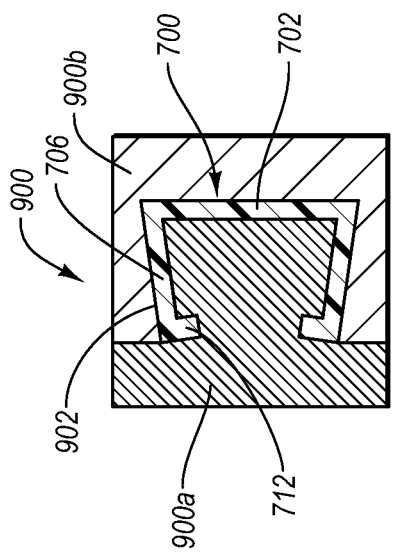
Figure 9B:
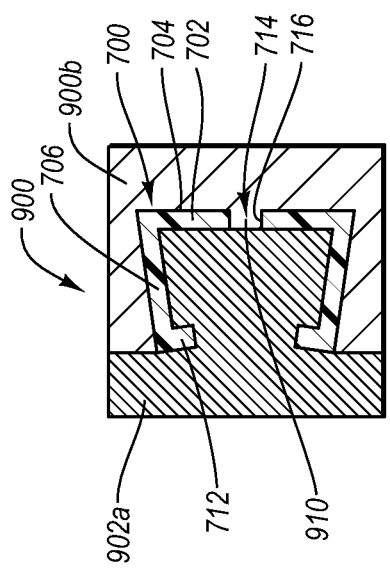

Referring to FIGS. 9A through 9C, the valve 700 may be formed in the top portion 702 according to the method illustrated. As shown in FIG. 9A, the sidewall 706 and top portion 702 may be formed, such as by a molding process. As is apparent in FIG. 8A, the mold 900 includes mold portions 900a, 900b combinable to form a cavity 902 that may be filled with a liquid polymer that becomes solid through a cooling or curing process. The cavity 902 may include surfaces 904a, 904b positioned on either side of the top portion 702 of the molded valved cover 700. In the illustrated embodiment, the surfaces 804a, 804b are planar. The mold portions 900a, 900b may be shaped such that the sidewall 706 are tapered or converge with distance from the top portion 702.

Referring to FIG. 9B, the aperture 716 for the valve 714 may then be formed in the top portion 702, such as by means of cutting tool 906, such as a rotating drill, punch, actuated blade, or the like. A mandrel 908 may be inserted within the cavity defined by the top portion 702 and sidewall 706 and urged against the top portion 702 for support during cutting of the aperture 716 and may then be removed to yield a valved cover 700 such as is shown in FIG. 9C. Referring to FIG. 9B', alternatively, the mold 900 may define a projection 910 secured to one of the mold portions 900a, 900b and extending through the top portion 702 during molding such that following the molding step of FIG. 9B', the aperture 716 is already formed.

Following formation of the valved cover 700 and the aperture 716, the upper surface 704 may assume an inverted or concave shape due to residual stresses within elastomeric polymer forming the valved cover 700. For example, in the illustrated embodiment, the upper surface 704 assumes a conical shape. As the upper surface 704 assumes an inverted or concave shape, deformation of the top portion 702 may also cause the aperture 716 to assume a tapered shape such that the diameter of the aperture 716 increases with distance from the upper surface 704. In a like manner the tapering of the sidewall 706 with distance from the top portion 702 may be reduced due to narrowing of the top portion 702 due to residual stresses within the top portion.

Referring to FIG. 10A, in an alternative method of manufacturing a valved cover 700 a mold 1000 may be used including mold portions 1000a and 1000b forming a cavity 1002 constraining the sidewall 706 to be substantially perpendicular to the top portion 702. As in the embodiments described hereinabove, the cavity 1002 may be filled with a liquid polymer that is allowed to harden due to cooling or curing to form a valved cover 700. Referring to FIG. 10B, the aperture 716 for the valve 714 of the valved cover 700 may be formed by means of a cutting tool 1004, such as a drill, punch, articulated blade, or the like. A mandrel 1006 may be positioned within the cavity defined by the top portion 702 and sidewall 706 and resist deformation of the top portion 702 during the cutting step. The mandrel 1006 may then be removed to yield a valved cover 700 such as is shown in FIG. 10C.

Referring to FIG. 10C, as with the embodiment of FIGS. 9A through 9C, cutting of the aperture 716 may result in deformation of the top portion 702 due to residual stresses within the valved cover 700. Deformation of the top portion 702 may result in the upper surface 704 becoming concave, such as the conical shape illustrated in FIG. 10C. Deformation of the top portion 702 may also result in the aperture 716 becoming tapered such that the diameter of the aperture 716 increases with distance from the upper surface 704.

The residual stresses may include an interim stress differential created before the formed valved cover 700 has substantially cooled. The interim stress differential may be created by, for example the temperatures of the molds near the valve portion 550, the thickness along the valve portion, other aspects of the mold and/or valve portion may be varied, or combinations thereof.

Figure 11A:
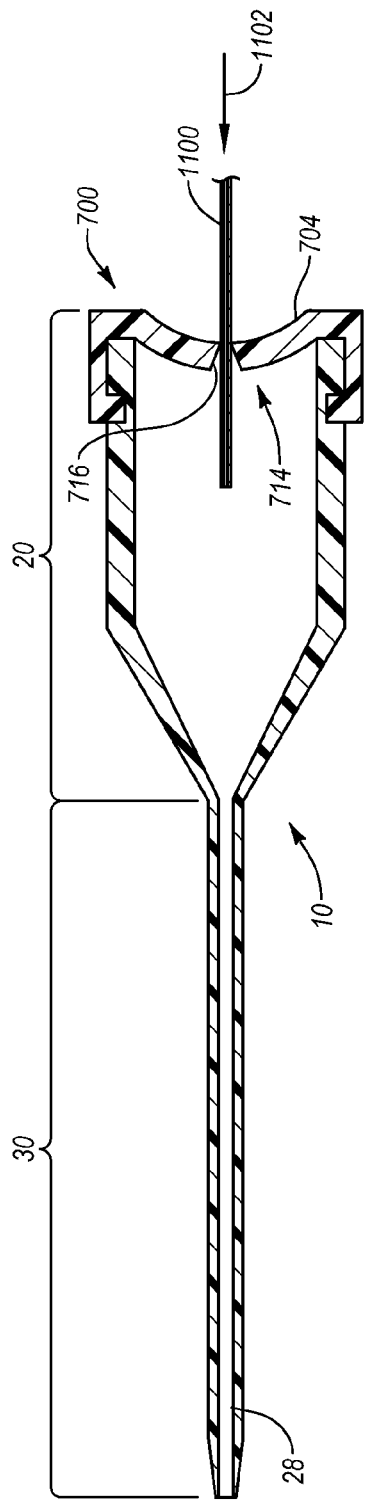
FIGS. 11A and 11B illustrate a method for using a valved cover in accordance with an embodiment of the present invention.
Figure 11B:
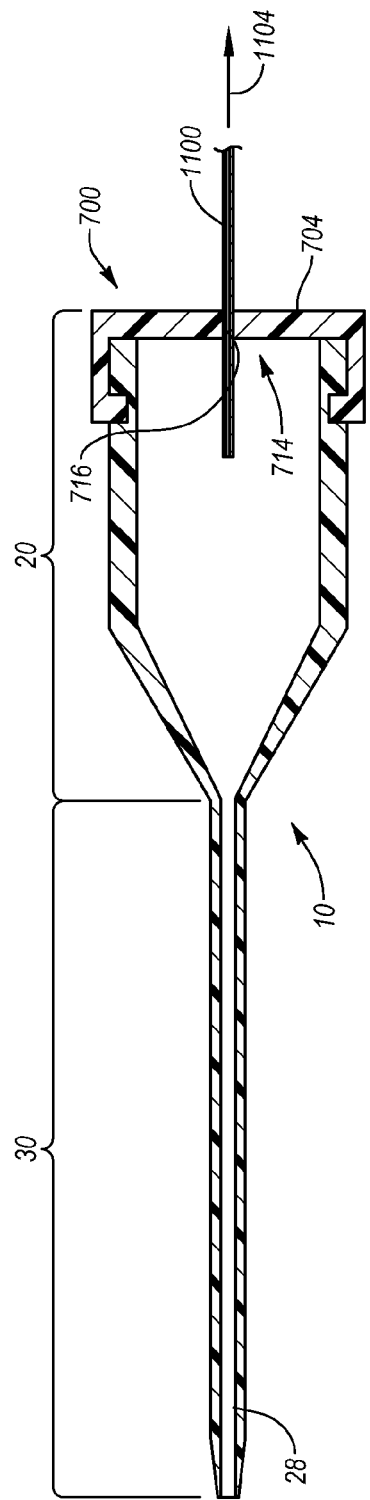

Referring to FIGS. 11A and 11B, a valved cover 700 having a concave or inverted upper surface 704 may be used to promote sealing with a catheter 1100 inserted through the valved cover 700 and through the hub 20 and tubular portion 30 of an introducer sheath bearing the valved cover 700. In one method of use, the catheter 1100 is inserted in a distal direction 1102 through the aperture 716 of the valve 714 and through the hub 20 and tubular portion 30, as shown in FIG. 11A. The catheter 1100 may then be drawn back slightly in proximal direction 1104 such that the concavity or inversion of the upper surface 704 is reduced. Urging the catheter 1100 slightly in the proximal direction 1104 may promote sealing by urging the walls of the aperture 716 against the catheter 1100 due to the tapered configuration of the aperture 716.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An introducer sheath, comprising:
   an elongate tubular portion having a longitudinal axis, the elongate tubular portion being elastically deformable about the longitudinal axis; and
   a hub portion, the hub portion having proximal end and a distal end, the proximal end being substantially wider than the distal end and the distal end secured to the elongate tubular portion;
   a valved cover elastically secured over the proximal end of the hub portion, the valved cover defining a non-planar outer surface in a relaxed state, the outer surface defining an aperture configured to receive a medical device.

2. The introducer sheath of claim 1, wherein the hub portion and the elongate tubular portion are formed as a unitary member.

3. The introducer sheath of claim 1, wherein the outer surface is substantially concave in the relaxed state.

4. The introducer sheath of claim 1, wherein the aperture includes a sealing surface.

5. The introducer sheath of claim 4, wherein the sealing surface is not generally parallel about a longitudinal axis through the aperture in the relaxed state.

6. The introducer sheath of claim 4, wherein the sealing surface is configured to form a seal between the medical device and the hub in a deformed state.

7. The introducer sheath of claim 1, wherein the aperture is tapered.

8. The introducer sheath of claim 7, wherein the aperture has a diameter that increases with distance from the outer surface.

9. An assembly comprising:
   an elongate tubular portion having a longitudinal axis, the elongate tubular portion being elastically deformable about the longitudinal axis; and
   a hub portion, the hub portion having proximal end and a distal end, the proximal end being substantially wider than the distal end and the distal end secured to the elongate tubular portion, the hub portion and elongate tubular portion defining a lumen; and
   a valved cover comprising a top portion extending transverse to the longitudinal axis and a sidewall portion extending from the top portion towards the distal end, the top portion and the sidewall portion collectively defining a cavity sized to elastically receive a portion of the hub portion, the valved cover further defining a valve in fluid communication with the lumen and configured to receive a medical device.

10. The assembly of claim 9, wherein one of an outer surface of the hub portion and an inner surface of the sidewall portion defines a circumferential groove and the other of the outer surface of the hub portion and the inner surface of the sidewall portion comprises a circumferential lip, the circumferential groove positioned to receive the circumferential lip when the hub portion is positioned within the cavity.

11. The assembly of claim 9, wherein an upper surface of the top portion has a concave shape and wherein the sidewall portion extends from a lower surface of the top portion.

* * * * *